United States Patent

Hirabayashi et al.

Patent Number: 6,114,693
Date of Patent: Sep. 5, 2000

[54] MASS SPECTROMETER AND MASS SPECTROMETRY METHOD FOR ANALYZING COMPOUNDS CONTAINED IN A SOLUTION

[75] Inventors: Atsumu Hirabayashi, Hachioji; Yukiko Hirabayashi, Kokubunji; Minoru Sakairi, Tokorozawa; Yasuaki Takada; Takayuki Nabeshima, both of Kokubunji; Hideaki Koizumi, Tokyo, all of Japan

[73] Assignee: Hitachi, Ltd., Tokyo, Japan

[21] Appl. No.: 09/299,638

[22] Filed: Apr. 27, 1999

Related U.S. Application Data

[63] Continuation of application No. 08/708,415, Sep. 5, 1996, Pat. No. 5,898,175.

[30] Foreign Application Priority Data

Sep. 7, 1995 [JP] Japan .................................. 7-229891

[51] Int. Cl.[7] .................................................. H01J 49/10
[52] U.S. Cl. ........................................................ 250/288
[58] Field of Search ................................. 250/288, 288 A

[56] References Cited

U.S. PATENT DOCUMENTS

| | | | |
|---|---|---|---|
| 4,298,795 | 11/1981 | Takeuchi et al. | 250/288 X |
| 4,300,044 | 11/1981 | Iribarne et al. | 250/282 |
| 4,861,988 | 8/1989 | Henion et al. | 250/288 |
| 4,935,624 | 6/1990 | Henion et al. | 250/288 |
| 4,977,785 | 12/1990 | Willoughby et al. | 250/288 X |
| 5,122,670 | 6/1992 | Mylchreest et al. | 250/288 X |
| 5,130,538 | 7/1992 | Fenn et al. | 250/282 |
| 5,170,052 | 12/1992 | Kato | 250/288 |
| 5,170,053 | 12/1992 | Hail et al. | 250/288 |
| 5,223,226 | 6/1993 | Wittmer et al. | 422/100 |
| 5,306,412 | 4/1994 | Whitehouse et al. | 204/299 R |
| 5,306,910 | 4/1994 | Jarrell et al. | 250/288 |
| 5,349,186 | 9/1994 | Ikonomou et al. | 250/288 |
| 5,376,789 | 12/1994 | Stenhagen | 250/288 |
| 5,423,964 | 6/1995 | Smith et al. | 204/452 |
| 5,559,326 | 9/1996 | Goodley et al. | 250/288 |

OTHER PUBLICATIONS

Hirabayashi et al., "Sonic Spray Ionization Method for Atmospheric Pressure Ionization Mass Spectrometry", *Analytical Chemistry*, vol. 66, No. 24, pp. 4557–4559, Dec. 1994.

M. Ikonomou et al., "Electrospray—Ion Spray: A Comparison of Mechanisms and Performance", *Analytical Chemistry*, vol. 63, No. 18, Sep. 15, 1991, pp. 1989–1998.

U.S. application No. 09/328,664 filed on Jun. 9, 1999.

B. Thomson et al., "Field induced ion evaporation from liquid surfaces at atmospheric pressure", *Journal of Chemical Physics*, vol. 71, No. 11, Dec. 1, 1979, pp. 4451–4463.

(List continued on next page.)

*Primary Examiner*—Jack Berman
*Attorney, Agent, or Firm*—Antonelli, Terry, Stout & Kraus, LLP

[57] ABSTRACT

A mass spectrometer comprising a passage through which a sample solution flows, the passage including a capillary having an open tip, the sample solution flowing through the capillary out of the open tip of the capillary, a gas passage which forms a gas flow around the open tip of the capillary, the gas flow spraying the sample solution flowing out of the open tip of the capillary, a first electrode which contacts the sample solution flowing in the passage and applies an electric potential to the sample solution flowing in the passage, a second electrode disposed around the capillary near the open tip of the capillary, the second electrode being downstream from the first electrode with respect to a direction in which the sample solution flows in the passage, there being no gap extending downstream from the open tip of the capillary to the second electrode in a direction in which the sample solution flows out of the open tip of the capillary, the second electrode being electrically isolated from the sample solution flowing in the capillary and applying an electric field to the sample solution flowing in the capillary, and an analyzer which analyzes a mass of gaseous ions formed from the sample solution sprayed by the gas flow.

11 Claims, 19 Drawing Sheets

OTHER PUBLICATIONS

H. Kambara, "Sample Introduction System for Atmospheric Pressure Ionization Mass Spectrometry of Nonvolatile Compounds", *Analytical Chemistry*, vol. 54, No. 1, Jan. 1982, pp. 143–146.

M. Yamashita et al., "Electrospray Ion Source. Another Variation on the Free–Jet Theme", *Journal of Physical Chemistry*, vol. 88, No. 20, 1984, pp. 4451–4459.

A. Bruins et al., "Ion Spray Interface for Combined Liquid Chromatography/Atmospheric Pressure Ionization Mass Spectrometry", *Analytical Chemistry*, vol. 59, No. 22, Nov. 15, 1987, pp. 2642–2646.

A. Cappiello et al., "Micro Flow Rate Particle Beam Interface for Capillary Liquid Chromatography/Mass Spectrometry", *Analytical Chemistry*, vol. 65, No. 9, May 1, 1993, pp. 1281–1287.

P. Kebarle et al., "From Ions in Solution to Ions in the Gas Phase—The Mechanism of Electrospray Mass Spectrometry", *Analytical Chemistry*, vol. 65, No. 22, Nov. 15, 1993, pp. 972 A–974 A.

A. Bruins, "Atmospheric–pressure–ionization mass spectrometry—II. Applications in pharmacy, biochemistry and general chemistry", *Trends in Analytical Chemistry*, vol. 13, No. 2, 1994, pp. 81–90.

A. Hirabayashi et al., "Sonic Spray Ionization Method for Atmospheric Pressure Ionization Mass Spectrometry", *Analytical Chemistry*, vol. 66, No. 24, Dec. 15, 1994, pp. 4557–4559.

M. Wilm et al., "Electrospray and Taylor–Cone theory, Dole's beam of macromolecules at last?", *International Journal of Mass Spectrometry and Ion Processes*, vol. 136, Nos. 2/3, Sep. 22, 1994, pp. 167–180.

U.S. application No. 08/404,615 filed on Mar. 15, 1995.

U.S. application No. 08/783,089 filed on Jan. 14, 1997.

SOLUTION

MASS SPECTROMETER AND MASS SPECTROMETRY METHOD FOR ANALYZING COMPOUNDS CONTAINED IN A SOLUTION

CROSS-REFERENCE TO RELATED APPLICATION

This application is a continuation of application Ser. No. 08/708,415 filed on Sep. 5, 1996, now U.S. Pat. No. 5,898,175.

BACKGROUND OF THE INVENTION

1. Field of the Invention

The present invention relates in general to a mass spectrometer and a mass spectrometry. Method, and more particularly to a mass spectrometer and a mass spectrometry method each of which employs an ion source for ionization entitled compounds contained in a solution.

2. Description of the Related Art

There is description of a sonic spray ionization method in an article of "Sonic Spray Ionization Method for Atmospheric Pressure Ionization Mass Spectrometry", *Analytical Chemistry,* Vol. 66, No. 24, Dec. 15, 1994, pp. 4557–4559. In the sonic spray ionization method, gas is caused to flow coaxially through a capillary from the outside of the capillary so as to spray the liquid through a tip of the capillary, thereby stably producing ions and charged droplets. In the case where the flow rate of gas at the tip of the capillary is substantially equal to the sonic velocity, an amount of positive and negative ions produced by the spray becomes maximum. In this case, neither an electric field nor discharge is applied to the liquid. The sprayed fine droplets thus produced are neutral in polarity as a whole and hence an amount of positive ions is substantially equal to an amount of negative ions.

In addition, there is description of an electrospray ionization method in an article entitled "Electrospray Ion Source. Another Variation on the Free-Jet Theme", *Journal of Physical Chemistry,* Vol. 88, No. 20, 1984, pp. 4451–4459, or U.S. Pat. No. 5,130,538. In the electrospray ionization method, a high voltage of 2.5 kV or more is applied to a metallic capillary into which the liquid is introduced and a counter electrode (corresponding in position to an inlet port for ions of a mass spectrometer). That is, the high voltage is applied to the liquid. As a result, the liquid is sprayed in the form of charged droplets through a tip of the capillary into a space in which an electric field is applied between the capillary and an counter electrode (the electrostatic spray phenomenon), thereby producing ions charged positive/negative from the charged droplets. In this connection, the polarity of the charged droplets and the ions matches the polarity of the applied voltage. In the electrospray ionization method, multiply-charged ions can be produced, and hence the electrospray ionization method is utilized for analysis of protein or the like in many cases. The flow rate of liquid is normally used in the range of 0.001 to 0.01 ml/min.

In addition, there is description of an ion spray ionization method in an article entitled "Ion Spray Interface for Combined Liquid Chromatography/Atmospheric Pressure Ionization Mass Spectrometry", *Analytical Chemistry,* Vol. 59, No. 22, Nov. 15, 1987, pp. 2642–2646, U.S. Pat. No. 4,861,988. In the ion spray ionization method, similarly to the electrospray ionization method, a high voltage of 2.5 kV or more is applied between the liquid at a tip of a spraying capillary and a counter electrode (corresponding in position to an inlet port for ions of a mass spectrometry unit). As a result, the liquid is sprayed in the form of ions and charged droplets through the tip of the capillary into a space in which an electric field is applied between the capillary and the counter electrode (the electrostatic spray phenomenon). In the ion spray ionization method, unlike the electrospray ionization method, gas is caused to flow into the outside of the spraying capillary in order to promote vaporization of the charged droplets. As a result, since the ions are produced utilizing the same electrostatic spray phenomenon, the ions thus produced are the same as those in the case of the electrospray ionization method at all. Thus, the polarity of the charged droplets and the ions matches that of the applied voltage. However, the flow rate of liquid is used in the range of 0.01 to 1 ml/min and it is larger than that in the electrospray ionization method. In addition, the flow rate of gas must not exceed 216 m/sec.

Further, there is description of an ionization method, in which when spraying liquid in the form of gas, a high voltage of 3.5 kV is applied to an electrode which is provided in the vicinity of a spraying portion, thereby producing charged droplets and ions, in an article entitled "Field induced ion evaporation from liquid surfaces at atmospheric pressure", *Journal of Chemical Physics,* Vol. 71, No. 11, Dec. 1, 1979, pp. 4451–4463, or U.S. Pat. No. 4,300,044. In this example, liquid and gas are respectively sprayed through an injection needle with 0.3 mm inner diameter. Unlike the sonic spray ionization method and the ion spray ionization method, however, the structure is adopted such that the direction of spraying the liquid is substantially perpendicular to the direction of the gas flow. The flow rate of the gas flow is not clear.

Now, when a mixture in solution is directly introduced to the mass spectrometer, it may be impossible in some cases to identify the mixture, since the resultant mass spectra are too complicated. For this reason, in the analysis of a mixture, a method is adopted in which the separation of the mixture in solution is firstly carried out using means such as a liquid chromatograph or a capillary electrophoresis system and the resultant extract is introduced into the mass spectrometer. That is, a liquid chromatograph/mass spectrometer and a capillary electrophoresis/mass spectrometer are present in each of which the separation and analysis of the mixture are realized online. In the liquid chromatograph, a solution is caused to flow through a column, which is packed with a material, by a pump at a fixed flow rate, thereby carrying out the separation of the mixture in solution. Therefore, an electric potential of the extract is the ground level. On the other hand, in the capillary electrophoresis system, a high voltage in the range of 20 to 30 kV or so is applied between the both ends of the capillary into which the solution is introduced, and then the mixture is separated on the basis of the electrophoresis. Normally, an electric potential at the outlet port side of the capillary is set to the ground level, and hence an electric potential of the extract is set to the ground level.

In the mass spectrometer, the analysis of the ion of interest is carried out on the basis of a value of m/z which is obtained by dividing the mass m of the ion by the charge number thereof z. The mass spectrometer in which the upper limit of the mass range of the mass spectrometry is very high is not suitable for practical use because of its large scale and its high cost. Therefore, in the general mass spectrometer, the upper limit of the mass range of the mass spectrometry is in the range of 1,000 to 2,000 or so in the value of m/z.

Now, in the above-mentioned prior art, the ions are mainly produced from the fine charged droplets. In the above-mentioned prior art relating to the electrospray ionization method and the ion spray ionization method, the charged droplets each having high density of electric charge are produced, and hence in the multiply-charged ions each having the charge state number z of 3 or more can be produced. Therefore, even in the case of the material, such as protein, having the giant mass m of several tens of thousands or so, the analysis thereof can be carried out since the value m/z is within the range of the mass spectrometry. However, the above-mentioned prior art relating to the sonic spray ionization method and the above-mentioned fourth prior art show a tendency in which the charged droplets each having low density of electric charge are produced and hence the ions each having the small charge state number are produced. That is, the production and the mass spectrometry of a singly-charged ion and a doubly-charged ion such as peptide can be made possible. However, in the analysis of the sample, such as protein, having the very large mass number m, since the multiply-charged ions each having the charge state number z of 3 or more can not be produced, the value of m/z departs from the mass range of the mass spectrometry and hence the mass analysis can not be carried out at all. This is a disadvantage.

In addition, in the above-mentioned prior art relating to the electrospray ionization method and the ion spray ionization method, the high voltage is applied to the liquid, and the ions and the charged droplets are produced on the basis of the electrostatic spray phenomenon. The large charged droplets each of which has low density of electric charge and the size of which is on the micron order as well as the fine charged droplets each having high density of electric charge are contained in the droplets which are produced on the basis of the above-mentioned phenomenon. The mass of the highly charged droplet is too large as compared with an amount of electric charge thereof, and hence it is difficult to control its movement by application of an electric field or a magnetic field. For this reason, when the mass spectrometry is carried out using a quadrupole mass spectrometer or a quadrupole ion trap mass spectrometer, the large charged droplets reach a detector without mass separation, and hence such droplets are detected in the form of random noises. In particular, the above-mentioned prior art relating to the ion spray ionization method shows a remarkable tendency that the highly charged droplets are readily produced since the flow rate of the liquid is high. The same problem is also applied to the above-mentioned fourth prior art. In the above-mentioned fourth prior art, the liquid is sprayed by assistance of the gas flow. However, the spraying portion adopts the structure such that the direction of spraying the liquid is substantially perpendicular to the direction of the gas flow. For this reason, a difference of the flow rate of the gas occurs between the upstream side of the gas flow and the downstream side of the gas flow at a tip of the injection needle through which the liquid is sprayed, and as a result, there arises a problem in dispersion in the droplet size that the size of the droplet becomes larger as the droplet is produced in the more downstream side. In addition, an electrode (an electrode 27 in FIG. 2 of U.S. Pat. No. 4,300,044) is constructed by one bar. For this reason, the density of electric charge of the droplet which is produced in a region, in the portion for spraying the liquid, in the vicinity of the electrode is different from the density of electric charge of the droplet which is produced in a region away therefrom. As a result, the large droplet having low density of electric charge is largely produced. In the above-mentioned fourth prior art, though the counter gas flow is generated at the inlet port for ions of the mass spectrometer in order to promote vaporization of the droplets, it is impossible to achieve the sufficient vaporization of the droplets. As described above, the ions are mainly produced from the fine charged droplet. In this connection, it is well known that the efficiency of producing ions is high as the size of the droplet is smaller. Then, the efficiency of producing ions from the large charged droplet is so low as to be able to be disregarded. As a result, there arises a problem that due to production of the large charged droplets, the sensitivity of detecting an ion is remarkably reduced by reduction of the intensity of a signal and increase of the noise level.

In addition, in the above-mentioned prior art relating to the electrospray ionization method and the ion spray ionization method, there is a problem, inherent in the electrostatic spray phenomenon, that it is necessary to adjust the position of the ion source whenever starting the spray in order to optimize the intensity of ions, and hence the operation for the system is complicated. This problem results from the fact that the electrostatic spray phenomenon shows the property that the shapes of the jet produced by spraying the solution vary remarkably due to contamination and wetting of the spraying capillary and the counter electrode (corresponding in position to the inlet port for ions of the mass spectrometry unit). Therefore, in the above-mentioned prior art relating to the electrospray ionization method and the ion spray ionization method, there arises a problem that the operation for the system requires a great deal of skill and hence the operating efficiency is extremely low.

In addition, in the above-mentioned prior art relating to the electrospray ionization method and the ion spray ionization method, in the case where the liquid chromatograph/mass spectrometer system or the capillary electrophoresis/mass spectrometer system is adopted in which the mixture separating means such as a liquid chromatograph or a capillary electrophoresis system is coupled to the upstream side thereof, since the high voltage is applied to the whole mixture separating means, there is a risk that during handling of the mixture separating means, an operator may get an electric shock in some cases. The electric potential of the whole mixture separating means may be set to the ground level when using the system in some cases. In such cases, the reproducibility of ion production and ion analysis is remarkably reduced since a sort of electrophoresis is realized in the capillary. For this reason, the liquid chromatograph/mass spectrometer system and the capillary electrophoresis/mass spectrometer system do not fulfill their functions in terms of operation as well as function. This is a problem.

In addition, each of the electrospray ionization method and the ion spray ionization method is a method wherein the voltage is directly applied to the sample solution, and by an electrostatic force occurring between the solution and the electrode of the mass spectrometer, the solution is sprayed so as to be ionized. Therefore, there arises a problem that when adding strong acid to the sample solution, since a current is caused to flow through the sample solution, no electrostatic spray phenomenon occurs and hence the ionization of the sample solution is difficult.

SUMMARY OF THE INVENTION

In view of the foregoing problems associated with the prior art, it is therefore an object of the present invention to provide a high sensitivity mass spectrometer method and a high sensitivity mass spectrometry employing a high efficiency ion source by which production and analysis of multiply-charged ions each having the charge state number of 3 or more can be realized in order to analyze a sample having the large mass number.

It is another object of the present invention to provide a high sensitivity mass spectrometer and a high sensitivity mass spectrometry method by which a large charged droplet resulting in reduction of the sensitivity of detecting ions is not produced too much.

It is still another object of the present invention to provide a high sensitivity mass spectrometer and a high sensitivity mass spectrometry method employing a high efficiency ion source which is excellent in operationalization.

It is yet another object of the present invention to provide a high sensitivity mass spectrometer and a high sensitivity mass spectrometry method employing a high efficiency ion source each of which is capable of setting an electric potential of liquid to the ground level, and is safe in operation and is capable of providing high reproducibility for the production and analysis of ions.

It is a further object of the present invention to provide a mass spectrometer and a mass spectrometry method employing an ion source in which even when subjecting a sample solution containing strong acid added thereto to mass spectrometry, a voltage is not directly applied to the sample solution so as for a current not to be caused to flow through the sample solution, and the electrostatic spray phenomenon is not utilized at all.

According to a first aspect of the present invention, there is provided a mass spectrometer employing an ion source including: a passage through which liquid is caused to flow to a predetermined position, at least a part of the passage being made of an insulating material; electric field applying means for applying a voltage to the liquid through the insulating material so as to generate an electric field applied thereto; and spray means for spraying therethrough the solution so as to produce charged gas, the spray means being arranged downstream with respect to the liquid to which the electric field is applied.

In addition, according to a second aspect of the present invention, there is provided a mass spectrometer including: separation means for separating sample liquid containing a mixture; a passage through which the sample liquid thus separated is caused to flow to a predetermined position, at least a part of the passage being made of an insulating material; electric field applying means for applying a voltage to the sample liquid through the insulating material so as to generate an electric field applied thereto; spray means as a room having a gas supplying unit for supplying gas, a gas supply port for supplying therethrough the gas from the gas supplying unit, an injection port for discharging therethrough the gas, and a holding portion for holding the passage; and analysis means, such as a quadrupole mass spectrometer or a quadrupole ion trap mass spectrometer, for subjecting the sprayed gas to mass spectrometry so as to analyze the sprayed gas.

In addition, according to a third aspect of the present invention, there is provided a mass spectrometer including: separation means for separating sample solution containing a mixture; detection means for detecting the characteristics of the separated sample solution; a passage through which the separated sample solution is caused to flow to a predetermined position, at least a part of the passage being made of an insulating material; electric field applying means for applying a voltage to the sample liquid through the insulating material so as to generate an electric field applied thereto; spray means as a room having a gas supplying unit for supplying gas, a gas supply port for supplying therethrough the gas from the gas supplying unit, an injection port for discharging therethrough the gas, and a holding portion for holding the passage; analysis means for subjecting the sprayed gas to mass spectrometry so as to analyze the sprayed gases; and a control unit for controlling both the electric field applying means and the analysis means on the basis of a signal outputted from the detection means.

According to a fourth aspect of the present invention, there is provided a mass spectrometer including: an injection port for spraying therethrough liquid so as to produce multiply-charged ions each being at least triply-charged, a part of or the whole injection port being made of an insulating material; a first electrode arranged in the periphery of the injection port; and a second electrode arranged opposite to the first electrode for generating a uniform electric field between the first electrode and the second electrode.

In addition, according to a fifth aspect of the present invention, there is provided a mass spectrometer having mixture separating means coupled thereto including: the mixture separating means for separating mixture; a metallic portion for determining an electric potential of the sample solution separated by the mixture separating means; a passage to which the liquid is supplied; electric field applying means for applying a voltage to the liquid flowing through the passage so as to generate an electric field applied thereto, the means being electrically insulated from the passage; an injection port for spraying therethrough the liquid by an ion source having spray means for spraying the liquid so as to produce charged droplets, so as to produce multiply-charged ions each being at least triply-charged, the injection port being arranged downstream with respect to the liquid to which the electric field is applied, a part of or the whole injection port being made of an insulating material; a first electrode arranged in the periphery of the injection port; and a second electrode arranged opposite to the first electrode for generating a uniform electric field between the first electrode and the second electrode.

In addition, according to a sixth aspect of the present invention, there is provided a mass spectrometry method wherein multiply-charged ions each being at least triply-charged are produced in a uniform electric field which is generated between a first electrode arranged in the periphery of an injection port for spraying therethrough liquid and a second electrode arranged opposite to the first electrode, and the resultant multiply-charged ions are analyzed by a mass spectrometry method unit.

In addition, according to a seventh aspect of the present invention, there is provided a mass spectrometry including the steps of: separating liquid; applying an electric field to the liquid which has been separated and is determined with an electric potential thereof; and passing multiply-charged ions each being at least triply-charged through a uniform electric field, which is generated between a first electrode arranged in the periphery of an injection port for spraying therethrough the liquid and a second electrode arranged opposite to the first electrode, so as to supply the multiply-charged ions to a mass spectrometry unit for carrying out mass analysis and also to subject the multiply-charged ions to mass spectrometry to analyze the multiply-charged ions.

In addition, according to a eighth aspect of the present invention, there is provided a mass spectrometry method including the electric field applying step of changing the polarity of an electric field applied to liquid in correspondence to the polarity of multiply-charged ions each being at least triply-charged which are produced in a uniform electric field generated between a first electrode arranged in the periphery of an injection port for spraying therethrough the liquid and a second electrode arranged opposite to the first electrode.

Further, according to a ninth aspect of the present invention, there is provided a mass spectrometry method including: the electric field applying step of changing the polarity of an electric field applied to liquid; and the step of producing multiply-charged ions, each being at least triply-charged and having the polarity varying in correspondence to the polarity of the electric field applied to the liquid, in a uniform electric field which is generated between a first electrode arranged in the periphery of an injection port for spraying therethrough the liquid and a second electrode arranged opposite to the first electrode.

In the conventional sonic spray ionization method, firstly, droplets each being electrically neutral are produced by spraying the liquid. While the positive ions and the negative ions which are substantially equal in the number to each other are contained in the droplet, the distribution of density of the positive and negative ions in the vicinity of the surface of the droplet is remarkably different from that in the central portion of the droplet due to the surface electric potential which is determined on the basis of combination of the droplet and the circumambient gases. In addition, the fine droplets are separated from the surface of the droplet by the gas flow of the sonic velocity. Since the number of positive ions is different from the number of negative ions in each of those fine droplets, the density of electric charge is low, but the fine droplet is charged positive or negative as a whole. The ions are produced on the basis of the process of evaporating ions from the fine charged droplet or the perfect vaporization of the charged droplet.

In the ionization method and the ion source of the present invention, the electric field is applied through the electrode arranged in the outside to the liquid which is introduced into the fused-silica capillary in the sonic spray ionization method. For example, when applying the negative voltage to the liquid, the density of the positive ions is much higher than the density of the negative ion in the area in the vicinity of the surface of the liquid. As a result, the droplets which are charged positive when spraying the liquid by assistance of the gas flow are preferentially produced, and hence the sprayed gas is charged positive. In the droplet, the positive ions are concentrated on the area in the vicinity of the surface by the Coulomb repulsion. The density of electric charge of the charged droplet is higher than the density of electric charge of the charged droplet which is produced by the normal sonic spray ionization method. In addition, at the time when the fine droplets are separated from the surface of the droplet by assistance of the gas flow of the sonic velocity, the fine droplets each having the very high density of electric charge are produced. As described above, it is well known that the ions are produced on the basis of the process of evaporating ions from the fine droplet or the perfect vaporization of the charged droplet. In the former, the efficiency of producing multiply-charged ions is in general remarkably so low as to be able to be disregarded as compared with that of producing singly-charged ions. However, in the case where the density of electric charge of the droplet is high, since the Coulomb repulsion in the droplet is remarkably large, the efficiency of producing multiply-charged ions becomes high. For this reason, the multiply-charged ions can also be produced. In the ionization method of the present invention, before the liquid has been sprayed, the density of positive or negative ions of the area in the vicinity of the surface of the liquid can be made very high. Therefore, it is meaningless that an electric field is applied to the droplets which have been produced by the spray. It is required that an electric field is applied to the liquid before being sprayed.

In addition, in the mass spectrometer and the mass spectrometry of the present invention, since the electrostatic spray phenomenon is not utilized for the ion production at all, the ion production is not influenced by the contamination and wetting of the inlet port for ions of the mass spectrometry unit and the spraying capillary at all. Therefore, the system can be readily handled, and the reproducibility of ion production is also high.

In addition, in the mass spectrometer system and the mass spectrometry of the present invention, the electric potential of the liquid introduced into the ion source can be set to the ground level. For this reason, the capillary electrophoresis system or the liquid chromatograph can be readily coupled to the portion of the system which is located upstream with respect to the ion source. In this connection, the reproducibility of the ion production is not degraded by this coupling at all.

As for a method of applying an electric field to the liquid from the outside, there is a method wherein a capillary is made of an insulating material such as quartz or resin, and a voltage is applied to a metallic orifice into which a tip of the capillary is inserted. As for another method, there is a method wherein a capillary is made of an insulating material, and an outer surface of a portion near a tip of the capillary is coated with metal, and under this condition, a voltage is applied to the outer surface of the capillary. In addition, there is also still another method wherein an insulating capillary is inserted into a metallic conduit to which a voltage is to be applied. In all methods, maintaining a distance between the surface of the liquid and the electrode constant is required for the ion production of high efficiency. In the case where the capillary is made of a conductive material such as metal, a high voltage needs to be applied to the electrode since the metallic capillary has the electrical shielding effect.

In the present invention, since the electric field is applied to the solution through the insulating material such as quartz or resin, the voltage is not directly applied to the solution. For this reason, even in the case where strong acid solution is applied to the mass spectrometry, no current is caused to flow through the solution. Further, since the solution is sprayed by assistance of the gas flow, the ion production is not hindered at all.

BRIEF DESCRIPTION OF THE DRAWINGS

The above and other objects as well as advantages of the present invention will become clear by the following description of the preferred embodiment of the present invention with reference to the accompanying drawings, wherein.

DESCRIPTION OF THE PREFERRED EMBODIMENTS

The preferred embodiments of the present invention will hereinafter be described in detail with reference to the accompanying drawings.

Figure 1:
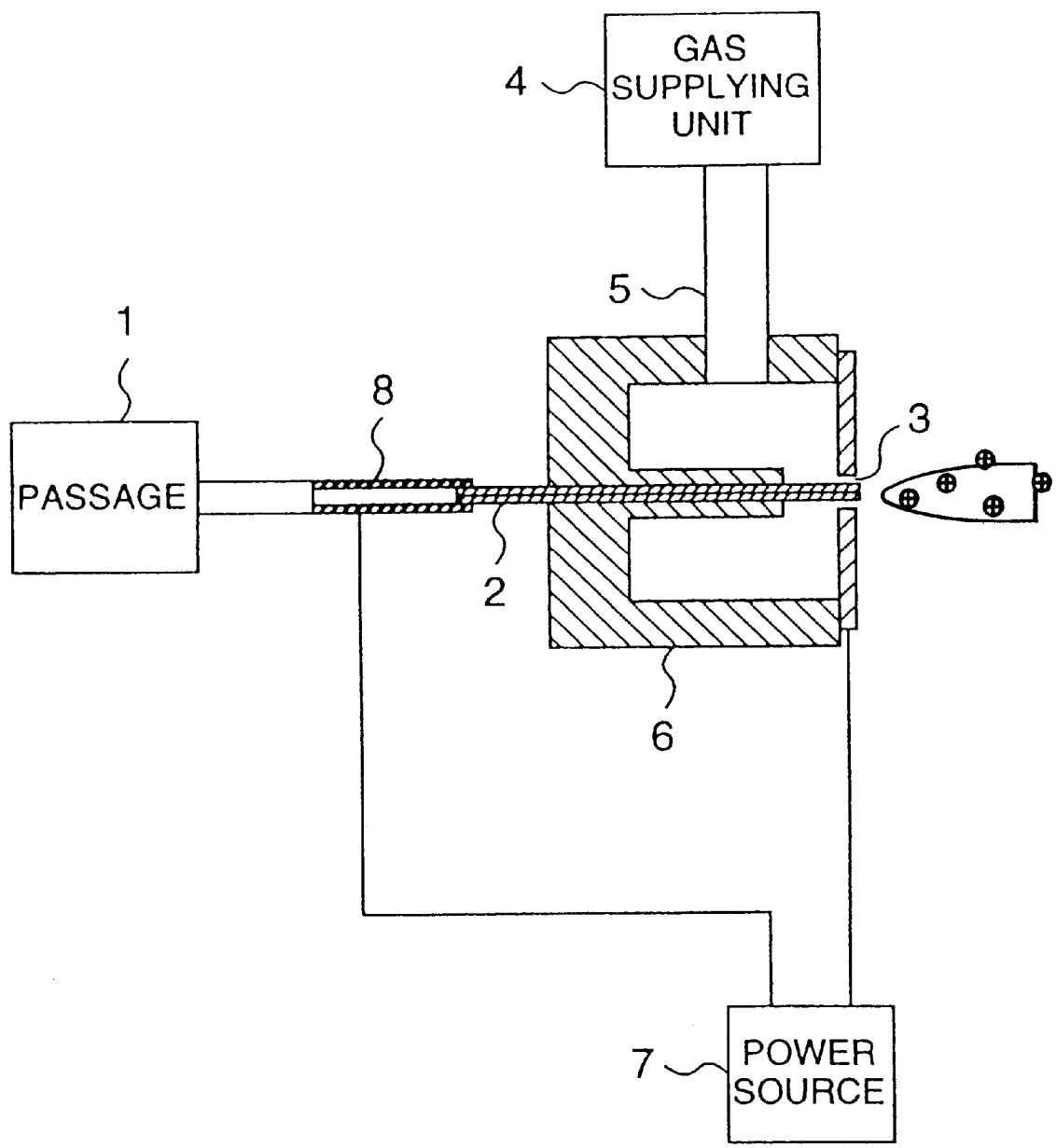
FIG. 1 is a schematic view, partly in cross sectional view, showing a structure of an ion source according to an embodiment of the present invention.

Referring first to FIG. 1, there is shown a schematic view, partly in cross sectional view, of a structure of an ion source according to an embodiment of the present invention. Liquid is introduced into a capillary 2 through a passage 1. A tip of the capillary 2 is substantially coaxially inserted into an orifice 3. Gases which has been supplied from a gas supplying unit 4 is introduced into an ion source body 6 through a gas introducing conduit 5 and then is discharged through the orifice 3 to the outside. The orifice 3 is made of metal, and a suitable voltage is applied across the orifice 3 and a metallic conduit 8 by a power source 7. Though no current is caused to flow between the orifice 3 and the liquid since electrical conduction is not established between the orifice 3 and the liquid, a suitable electric field is applied to the liquid. The liquid which has reached at the tip of the capillary 2 is sprayed by assistance of the gas flow. Ions and fine charged droplets are produced in the sprayed gas.

Figure 2:
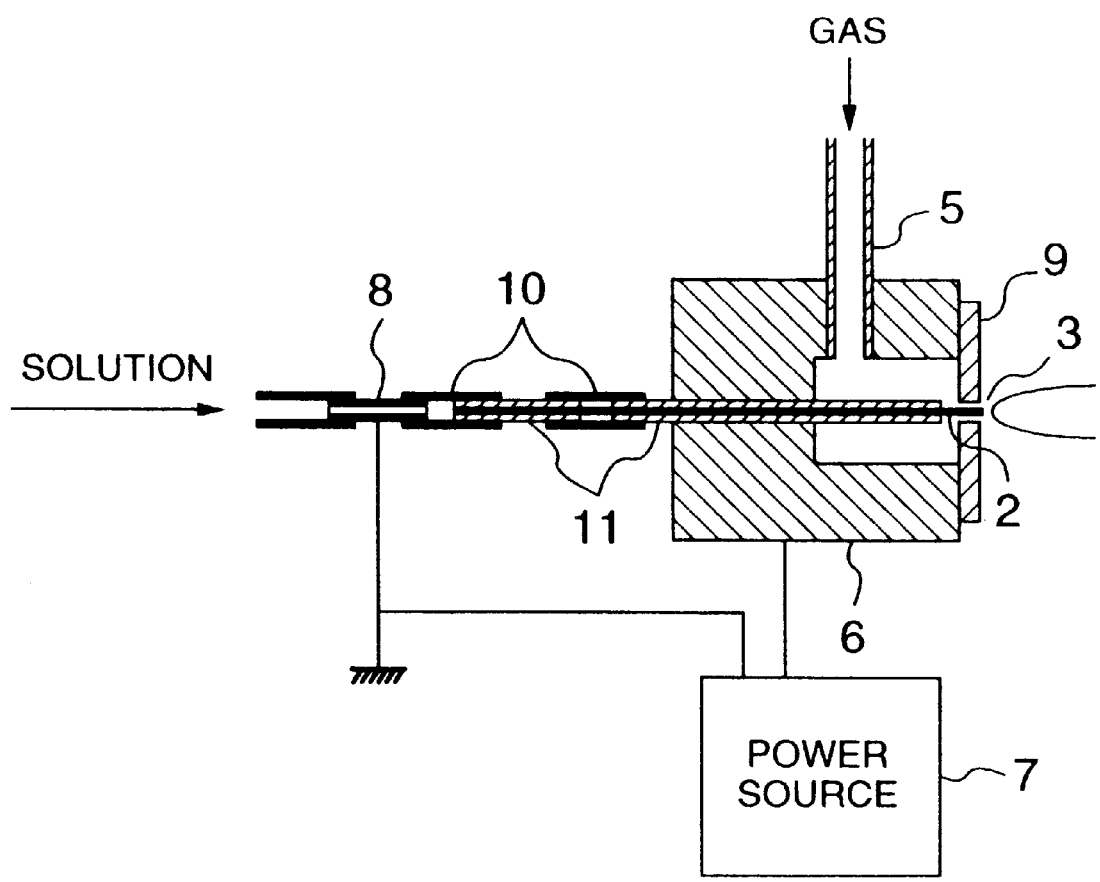
FIG. 2 is a cross sectional view, partly in block diagram, showing a structure of an ion source according to an embodiment of the present invention.

Referring to FIG. 2, there is shown a cross sectional view, partly in block diagram, of an ion source according to an embodiment of the present invention. After having been introduced into the metallic conduit 8, an electric potential of which is set to the ground level, at a flow rate of 5 to 100 μl/min, the liquid is introduced into a fused-silica capillary 2 (its inner diameter is 1.0 mm and its outer diameter is 0.2 mm). An orifice plate 9 through which an orifice 3 (its inner diameter is 0.4 mm and its outer diameter is 1.0 mm) is bored is made of duralumin, and a suitable voltage is applied to the orifice plate 9 by the power source 7. The capillary 2 is inserted into two Teflon conduits 10 and two stainless conduits 11, and is adhered to the stainless conduits 11 by adhesive. In addition, the liquid is electrically insulated from the ion source body 6 through a space defined between the two stainless conduits 11. The central axis of the capillary 2 is substantially aligned with the central axis of the orifice 3, and a tip of the capillary 2 is exposed from the orifice plate 9 to the outside by about 0.2 mm. The stainless conduits 11 are also used to fix the capillary 2 to the ion source body 6. When the orifice plate 9 is cooled by the adiabatic expansion of the gases, the resultant droplet may coagulate so that they may not become fine in some cases. As a result, since large charged droplets are produced, an amount of ions is reduced. This problem is avoided in such a way that a heater is provided in either the orifice plate 9 or the ion source body 6 in order to heat it, or the gas to be introduced into the ion source is previously heated. The gas are introduced into the gas introducing conduit 5 from a gas bomb or a gas compressor. A gas flow rate regulating unit such as a mass flow controller or a purge meter is installed in the middle position between the gas bomb or the gas compressor and the gas introducing conduit 5 in order to regulate the flow rate of gas for use in the spraying operation. When the gas flow rate is just 3 l/min, the flow rate of gas in the vicinity of the tip of the capillary 2 becomes the sonic velocity.

It is well known that the ions are produced from the fine charged droplets with 10 nm or less diameter. In the present embodiment, similarly to the sonic spray ionization method, the fine charged droplets are produced by assistance of the gas spray. While the size of the average droplet which is produced by assistance of the gas spray is decreased as the gas flow rate is further increased, the size of the average droplet is increased when the gas flow rate becomes supersonic. This results from the fact that the shock wave is generated (refer to FIG. 9). Therefore, the size of the average droplet becomes minimum when the gas flow rate is the sonic velocity, and hence the ion production is most efficiently carried out. The efficiency of producing fine droplets is high, and as a result, the efficiency of producing ions is high as a wall thickness of the capillary 2 is smaller.

For production of the gas flow of the sonic velocity, if an ambient pressure of the ion source is 1 atmosphere and also a thickness of the orifice 3 can be disregarded, the portion located upstream with respect to the orifice 3 requires a gas pressure of about 2 atmospheres. However, there may be a case where the pressure reduction within the orifice 3 cannot be disregarded in correspondence to the thickness of the orifice plate 9. If a suitable pressure gauge is provided in the ion source body 6 so as to regulate the gas pressure to produce the gas flow of the sonic velocity, this is so convenient. In this case, it is likely to be more acceptable that the pressure is regulated so as to apply a gas pressure in the range of 0.5 to 5 atmospheres or so to the portion located upstream with respect to the orifice 3. In addition, it is also suitable for practical use that the gas flow of the sonic velocity is generated by gas flow rate regulating means such as a purge meter or a mass flow meter. If the thickness of the orifice 3 is too large, the pressure reduction within the orifice 3 is increased and as a result the pressure within the orifice 3 needs to be unnecessarily increased. There is no need of making the thickness of the orifice 3 larger than a wall thickness of the ion source body 6. Conversely, if the thickness of the orifice 3 is too small, the orifice 3 cannot withstand a pressure difference between the inside and the outside of the ion source body 6 in terms of strength. For this reason, it is suitable for practical use that the thickness of the orifice 3 is set to the range of 0.5 to 1 mm which is larger than the diameter of the capillary 2. A portion of the ion source body 6 located upstream with respect to the orifice 3 requires a space acting as a gas reservoir so as not to decrease the gas pressure therein. This space requires the size which is 5 or more times as large as that of the diameter of the capillary 2.

Figure 3:
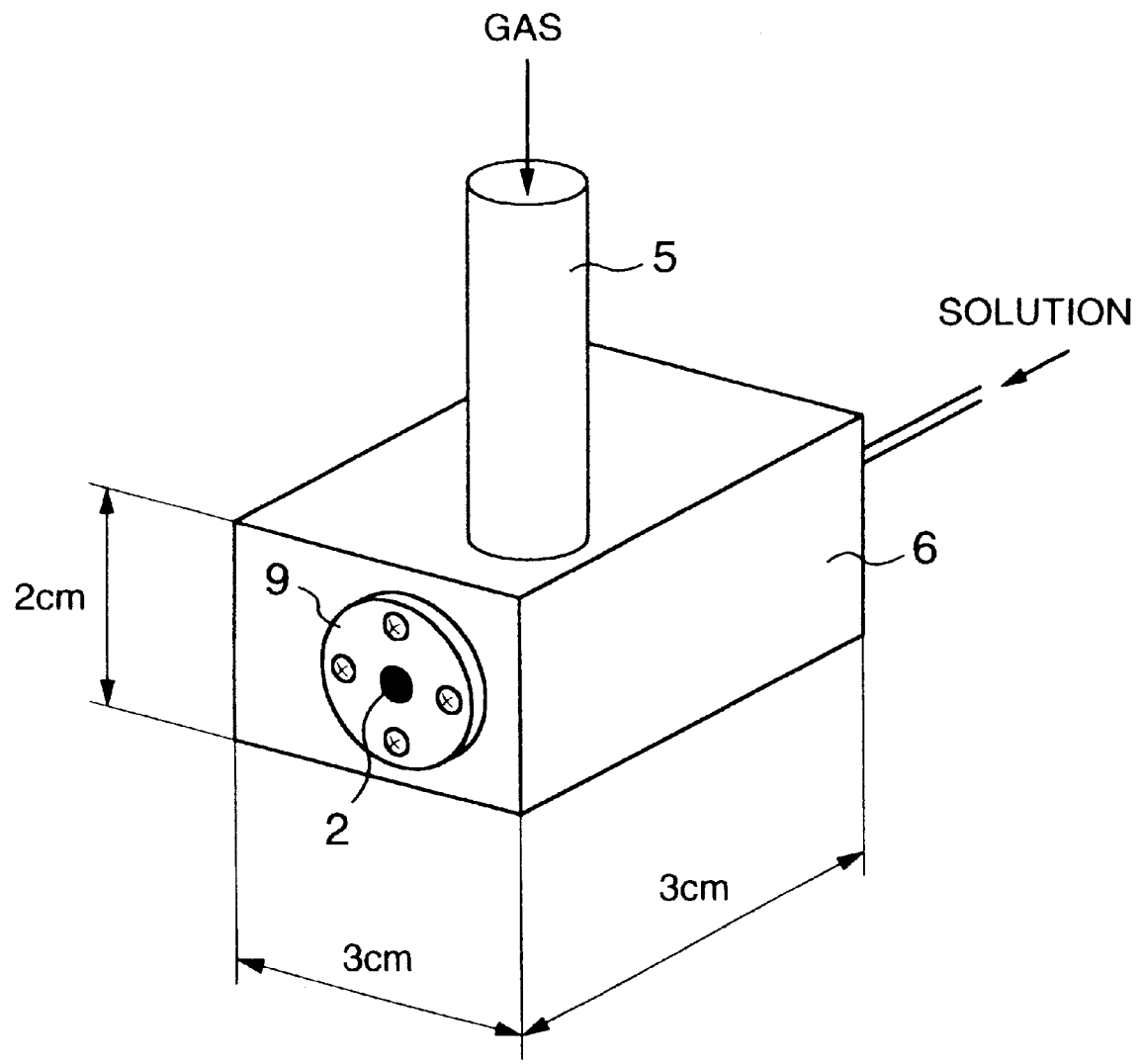
FIG. 3 is a perspective view showing a structure of an ion source according to the embodiment of the present invention shown in FIG. 2.

Referring to FIG. 3, there is shown a sketch drawing of the ion source according to the embodiment of the present invention shown in FIG. 2. The sprayed gases are discharged to this side in the figure. While a cross section of the ion source body 6 when viewed perpendicularly to the central axis of the capillary 2 is a quadrangle, it may also be made a round shape. The orifice plate 9 has four holes bored therethrough in addition to the orifice 3, and the orifice plate 9 is screwed on the ion source body 6 by using four screws corresponding to the four holes. The positional adjustment is carried out under the microscope such that the center of the orifice 3 is substantially aligned with the center of the capillary 2, and under this condition, the orifice plate 9 is mounted to the ion source body 6 by the four screws. In such a way, a uniform gas flow is generated at the tip of the capillary 2. From the size in the figure, it is shown that the ion source of the present invention is very compact.

Figure 4:
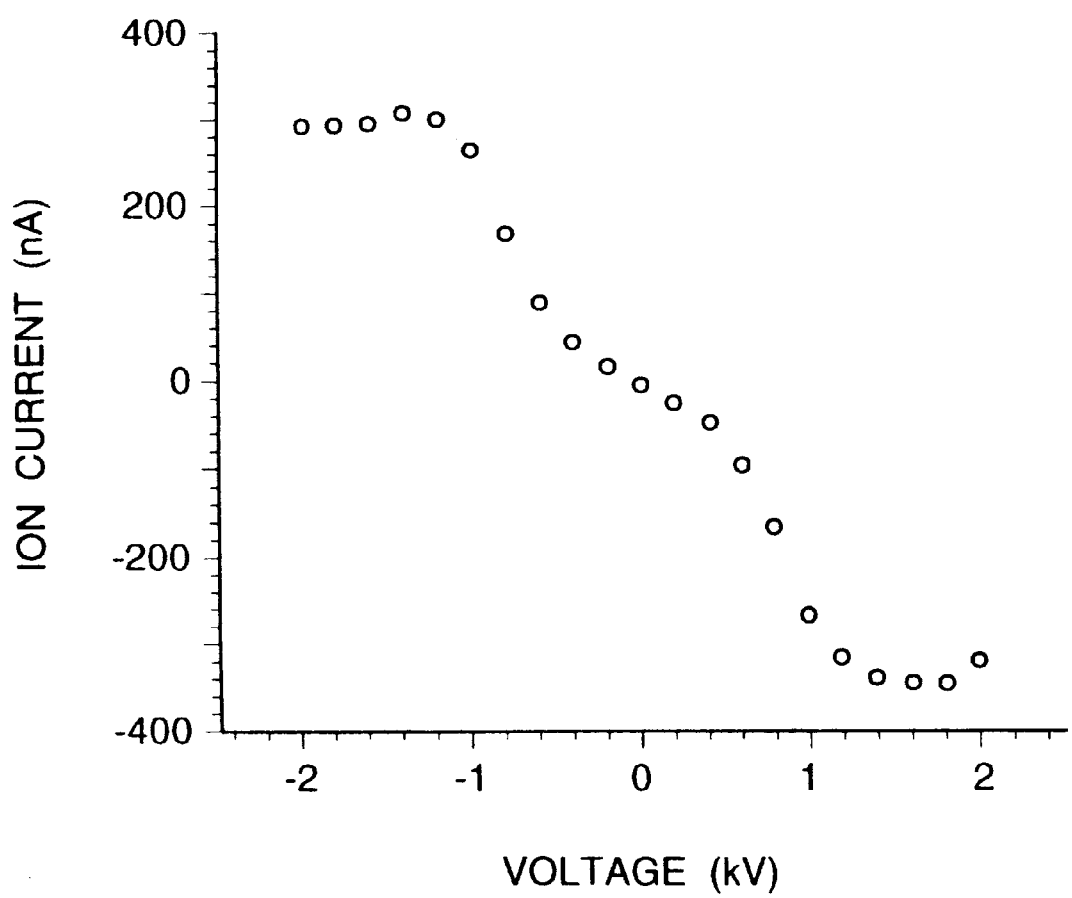
FIG. 4 is a graphical representation showing the relationship between a voltage applied to an orifice and a total ion current.

Referring to FIG. 4, there is shown the dependency of the total ion current produced by the spray on a voltage applied to the orifice 3. This is obtained from the experimental results in the case where a solution of 47.5% methyl alcohol/47.5% water/5% acetic acid is used as the sample liquid. From the experimental results, it is shown that when applying a positive voltage to the sample solution, the negative ions and charged droplets are produced, while when applying a negative voltage thereto, the positive ions and charged droplets are produced. That is, it is shown that if applying a voltage of the polarity opposite to the polarity of the ions which are intended to be produced, the ions of the desired polarity are produced. In addition, it is shown that while the total ion current is decreased along with increase of the applied voltage when the absolute value of the applied voltage is equal to or smaller than 1 kV, the total ion current is not changed too much to be saturated when the absolute value of the applied voltage is equal to or larger than 1 kV. This phenomenon shows that the density of ions of the same polarity in the vicinity of the surface of the liquid just before being sprayed reaches the limit. Therefore, it is suitable for practical use that the absolute value of the applied voltage is set to the range of 1 kV to 2 kV on the basis of the experimental results.

Now, assuming that the electric conductivity of the liquid is sufficiently high, an electric potential at a portion in the vicinity of the central axis of the capillary 2 can be regarded as 0V, and also the intensity of an electric field can be estimated as 5,000 kV/m (=1,000V/0.2 mm). Therefore, either in the case where an inner diameter of the orifice 3 is larger, or in the case where an electrode is provided in the position more apart therefrom, a higher voltage needs to be applied.

Figure 5:
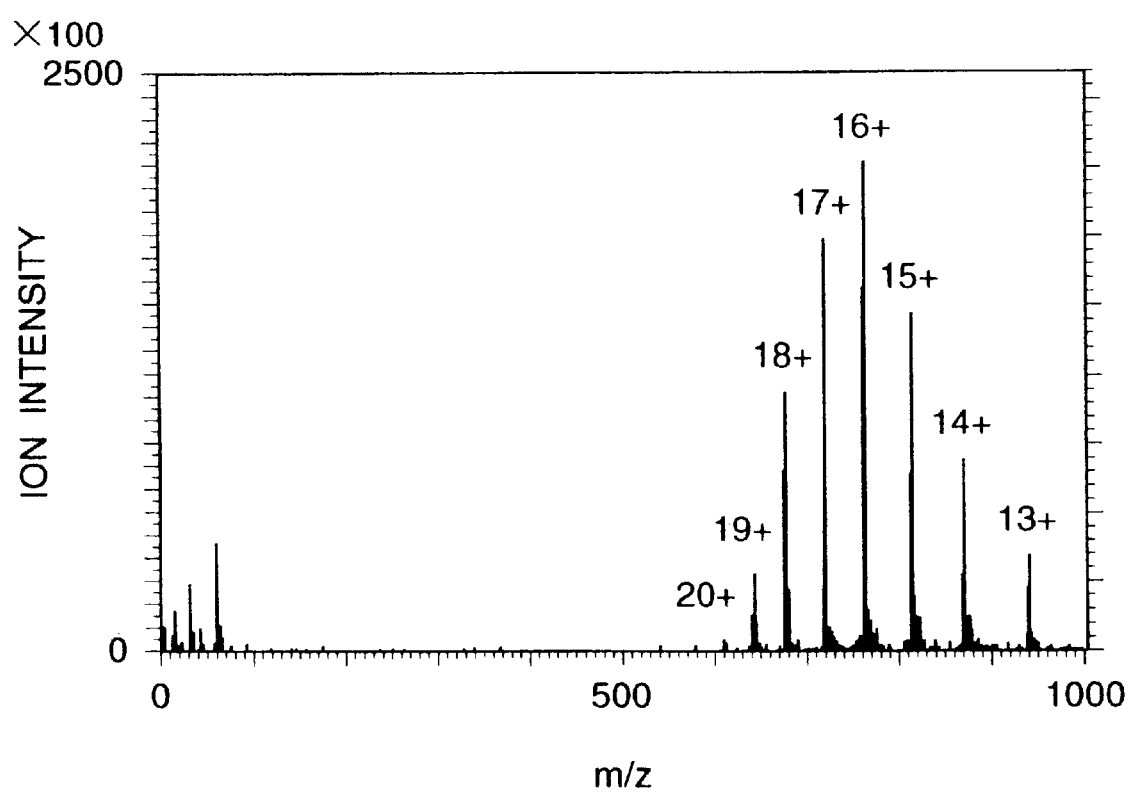
FIG. 5 is a mass spectrum which is obtained from a cytochrome-C solution.

Referring to FIG. 5, there is shown a mass spectrum which is obtained from the experimental results in which ions produced when setting the applied voltage to −1 kV is subjected to the mass spectrometry. That is, this is obtained from the experimental results in which a solution of cytochrome-C with 1 $\mu$mol/l concentration (a kind of protein, and its molecular weight is about 12,500) (a solvent is 48% methyl alcohol liquid containing 5% acetic acid added thereto) is introduced into the capillary 2 at a flow rate of 30 $\mu$l/min, and the ions which have been obtained by spraying the solution by assistance of the gas flow of the sonic velocity are analyzed using a quadrupole mass spectrometer. From the mass spectrum, it is shown that a series of multiply-charged ions ranging from a 13+ ion to a 20+ ion are clearly detected in an area of m/z equal to or lower than m/z=1,000 with a 16++ ion (m/z =766), in which sixteen protons are added to a cytochrome-C molecule, as center.

Figure 6:
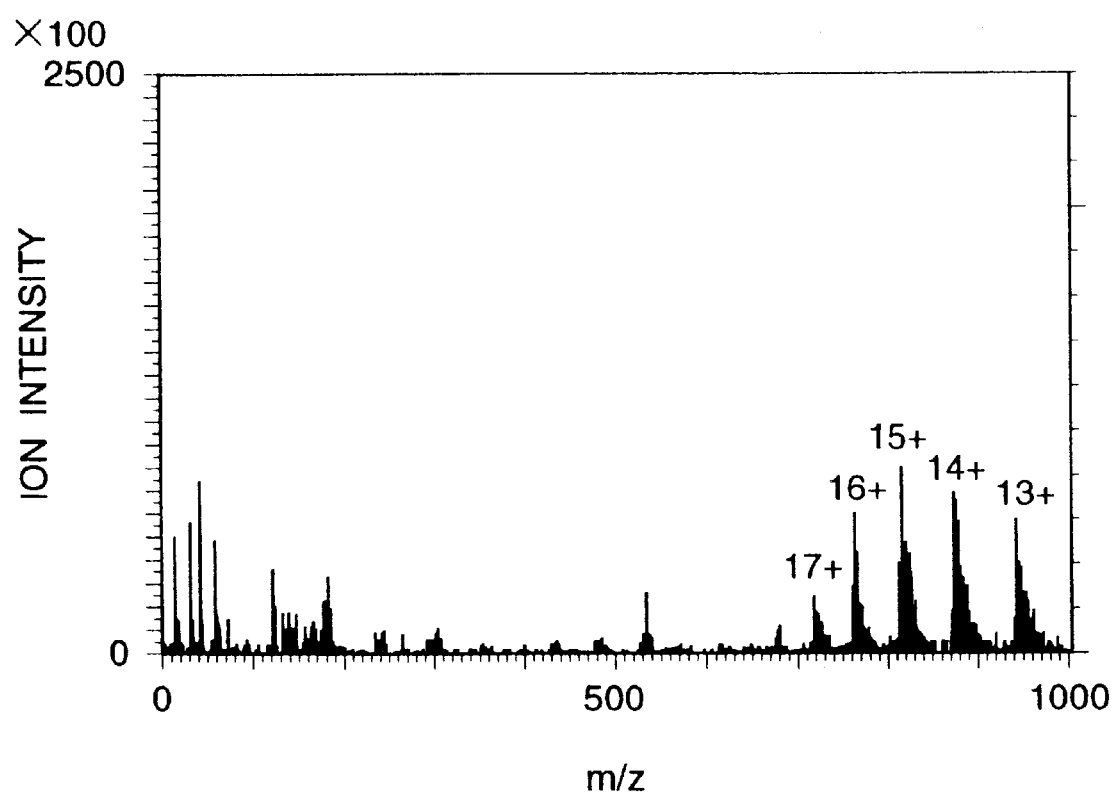
FIG. 6 is a mass spectrum which is obtained from a cytochrome-C solution by the ion spray ionization method.

Heretofore, the ion spray ionization method and the electrospray ionization method (the principle of producing ions is substantially the same with the two methods) have been utilized for production of multiply-charged ions. Then, the ions are produced from the same cytochrome-C solution as the above-mentioned solution by utilizing the ion spray ionization method, and the resultant ions are detected by the same quadrupole mass spectrometer. These experimental results are shown in the form of a mass spectrum in FIG. 6. The axis of ordinate is the same as that in FIG. 5. From FIG. 6, it is shown that with respect to the multiply-charged ions, the same spectrum pattern of the mass spectrum as that in FIG. 5 is obtained, but the ion intensity is about 2.6 times as low as that of the experimental results shown in FIG. 5. This corresponds to the ion detection sensitivity which is obtained when the applied voltage is set to about 700V in the ion source of the present invention. In addition, from FIG. 6, it is shown that the noise level is much higher than that shown in FIG. 5. Those noises result from the fact that the larger charged droplets are produced in large quantities by the ion spray ionization method as compared with the ionization method of the present invention, and those larger charged droplets are detected in the form of random noises. In FIG. 6, the S/N ratio is about 9 times as small as that of FIG. 5. As a result, it is shown that when utilizing the ionization method of the present invention shown in FIG. 5, the ion detection of higher sensitivity can be carried out. In addition, in FIG. 6, many ions resulting from the solvent are detected in the area of m/z equal to or lower than m/z=300. The analysis of such a complicated mass spectrum requires experience.

Figure 7:
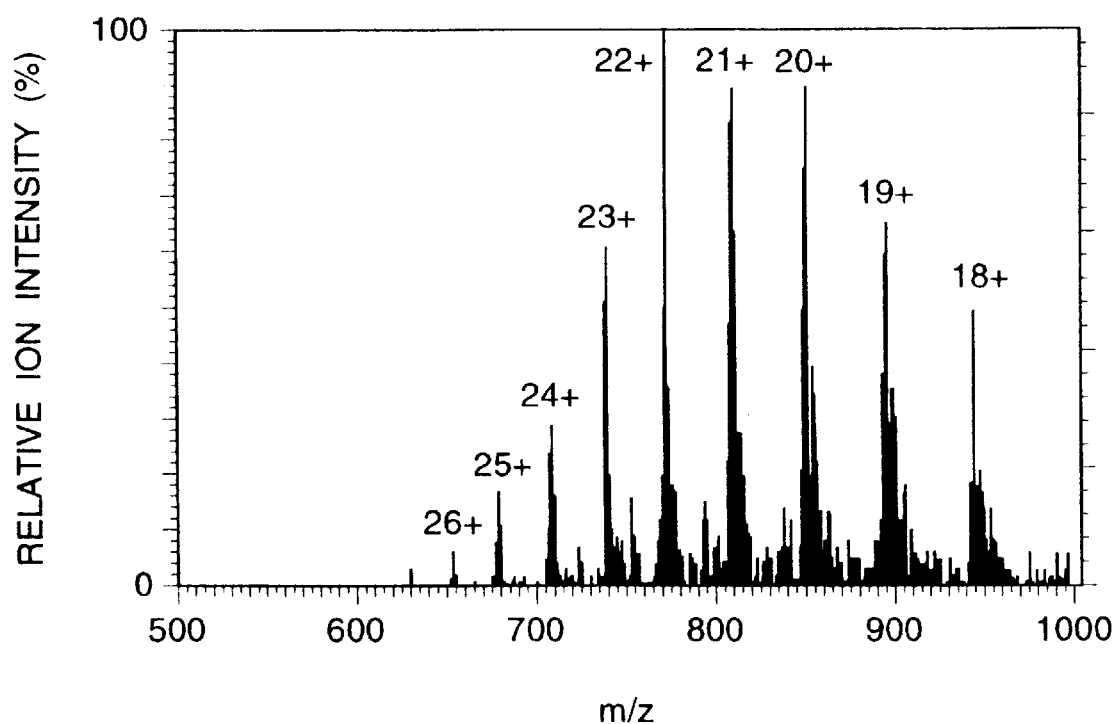
FIG. 7 is a mass spectrum which is obtained from a myoglobin solution.
Figure 8:
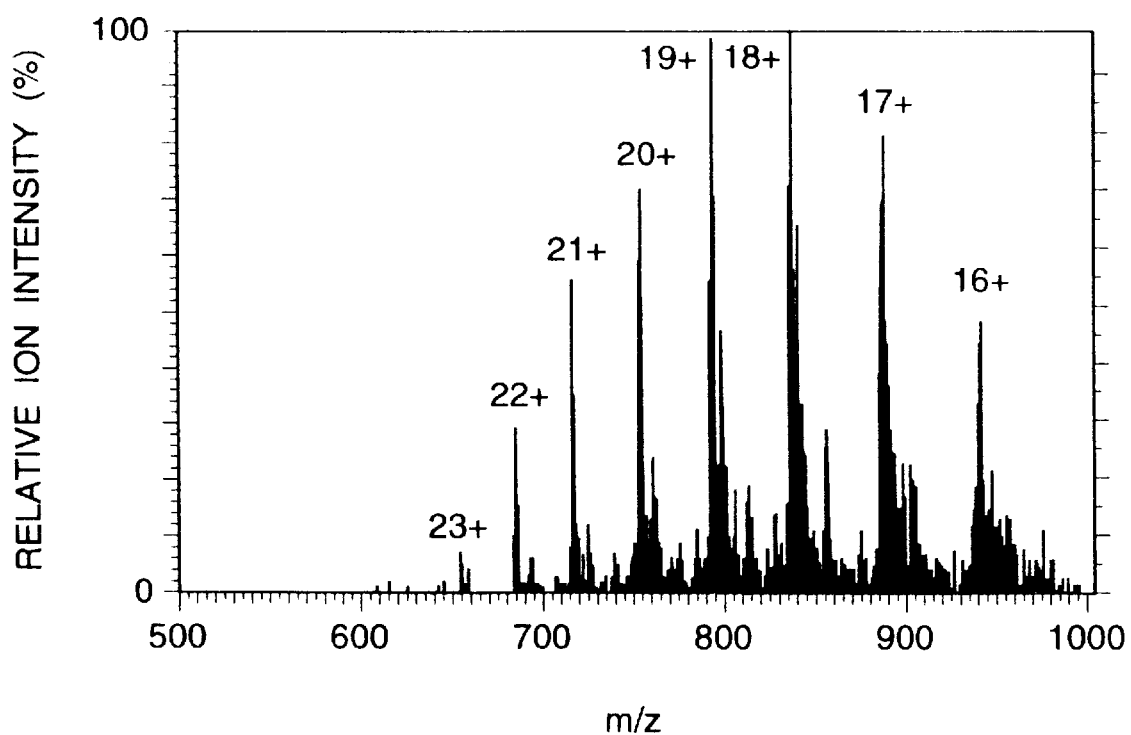
FIG. 8 is a mass spectrum which is obtained from a hemoglobin solution.

Referring to FIG. 7, there is shown a mass spectrum which is obtained from a myoglobin solution (the concentration is 1 $\mu$mol/l, and a solvent is 48% methyl alcohol containing 5% acetic acid added thereto). Referring to FIG. 8, there is shown a mass spectrum which is obtained from a hemoglobin solution (the concentration is 1 $\mu$mol/l, and a solvent is 48% methyl alcohol containing 5% acetic acid added thereto). Myoglobin has the molecular weight of 17,200, and from the myoglobin solution, a series of multiply-charged ions ranging from a 18+ ion to a 26+ ion are detected, with a 22+ ion (m/z=772), which has twenty-two protons added thereto, as center. Hemoglobin is a kind of protein with 64,500 molecular weight in which two kinds of sub-units are contained, and for every kind of sub-unit, the two associated sub-units are coupled to each other. In FIG. 8, the mass spectrum of the sub-units is observed.

Figure 9:
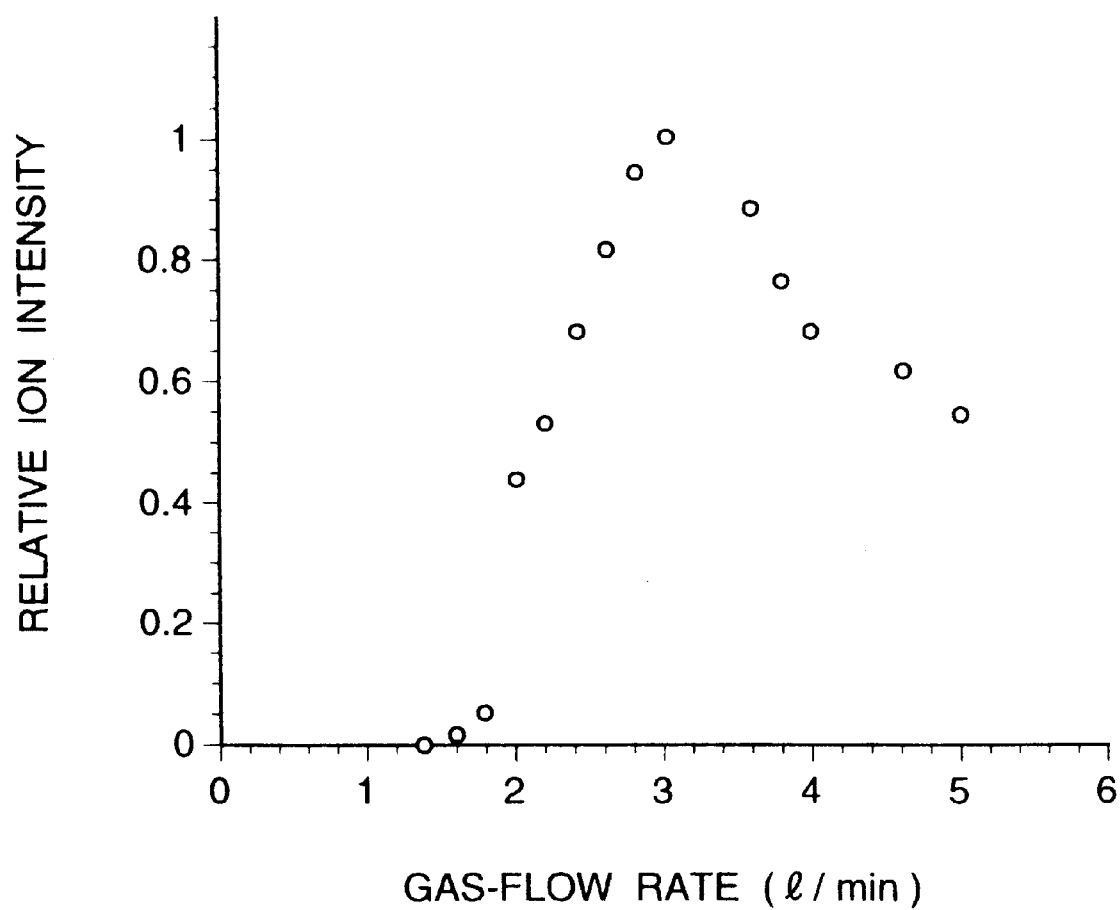
FIG. 9 is a graphical representation showing the relationship between a flow rate of sprayed gases and the relative ion density.

Referring to FIG. 9, there is shown the dependency of the flow rate F of the sprayed gas on the relative intensity of the 16+ ion in FIG. 5. There is used herein the ion source of the embodiment shown in FIG. 2. From the graphical representation, the relationship is obtained in which the relative ion intensity is increased along with increase of the flow rate of gas. In the present experiments, it is previously known that the flow rate of gas corresponds to the sonic velocity (Mach 1) when the flow rate of gas is about 3 l/min, and the flow rate of gas is equal to or lower than Mach 2 when the flow rate of gas is about 7 l/min (refer to the above-mentioned first article from *Analytical Chemistry*, Vol. 66, No. 24, Dec. 15, 1994, pp. 4457–4559). From the figure, it is shown that while no ion is produced when the flow rate of gas is equal to or lower than 1.4 l/min, and the relative ion intensity is increased along with increase of the flow rate of gas, the relative ion intensity becomes maximum when the flow rate of gas is about 3 l/min, and the relative ion intensity is decreased due to generation of the shock wave when the flow rate of gas is equal to or higher than about 3 l/min (the supersonic area). Thus, while the dependency of the relative ion intensity on the gas flow rate of the present invention is similar to that utilizing the conventional sonic spray ionization method, it is the feature inherent in the present invention that the sprayed gas which is produced from the ion source of the present invention is charged positive or negative as a whole.

Now, as described above, the flow rate of gas may be controlled by regulating the gas flow rate F using the flow rate regulating means. In the example of the ion source shown in FIG. 2, an area S of a cross section of a clearance gap defined between the orifice and the capillary when viewed perpendicularly to the capillary is calculated to be $9.4 \times 10^{-8}$ m$^2$. If the flow rate of gas is under the standard state (i.e. standard conditions) (20° C., 1 atmosphere), a ratio of F/S is estimated to be 250 m/sec when F is 1.4 l/min, and it is estimated to be 1,200 m/sec when F is 7 l/min. In this connection, take notice of the fact that the unit of the ratio F/S is velocity, but the ratio F/S is different from the flow rate of gas.

The flow rate of gas may be controlled by the gas pressure within the ion source. In FIG. 9, the production of the ions is started at a pressure of about 1.2 atmospheres. Assuming that the isoentropic flow is established, in the case where the thickness of the orifice is sufficiently small, Mach about 0.5 is achieved when the gas pressure is 1.2 atmospheres, and Mach 1 is achieved when the gas pressure is 2 atmospheres. The gas pressure of 7.2 atmospheres is required for achieving Mach 2. By the way, the gas pressure of 40 atmospheres is required for achieving Mach 3, and hence in this case, there is a problem in terms of practical use. In order to control the flow rate of gas by the gas pressure, it is suitable for practical use that the gas pressure is regulated in the range of 0.5 to 5 atmospheres.

In this ion source, a diameter of the orifice is 0.4 mm, and an outer diameter of the fused-silica capillary is 0.2 mm. Therefore, the area S of the cross section of the clearance gap defined between the orifice and the capillary is calculated to be $9.4 \times 10^{-8}$ m$^2$. Then, when employing the parameter F/S, the parameter F/S is 250 m/sec when the flow rate F of gas is 1.4 l/min, and F/S is 530 m/sec when F is the sonic velocity (notice needs to be taken of the fact that while the unit of the parameter F/S is velocity, it has no relation to the actual flow rate of gas). Even if the flow rate F of gas is increased up to 7 (F/S=1,200 m/sec) or more, the consumption of gas is increased only, and the efficiency of producing ions is not increased. For this reason, actually, the parameter F/S is used in the range of 250 to 1,200 m/sec. Since the area S is determined by the structure of the ion source, it is convenient that the flow rate F of gas is regulated using a flow controller such as a mass flow meter or a purge meter.

The gas flow is used to assist the spray of the liquid. Therefore, the kind of gas does not hardly participate in the ion production. Actually, it is convenient to use nitrogen gas as the gas used to produce the gas flow because nitrogen gas is inexpensive, and also is effective to vaporize the droplets since nitrogen gas is dry. In addition to nitrogen gas, even when using air, oxygen gas, carbon dioxide gas, rare gas, or the like, the same effect can be obtained.

Figure 10:
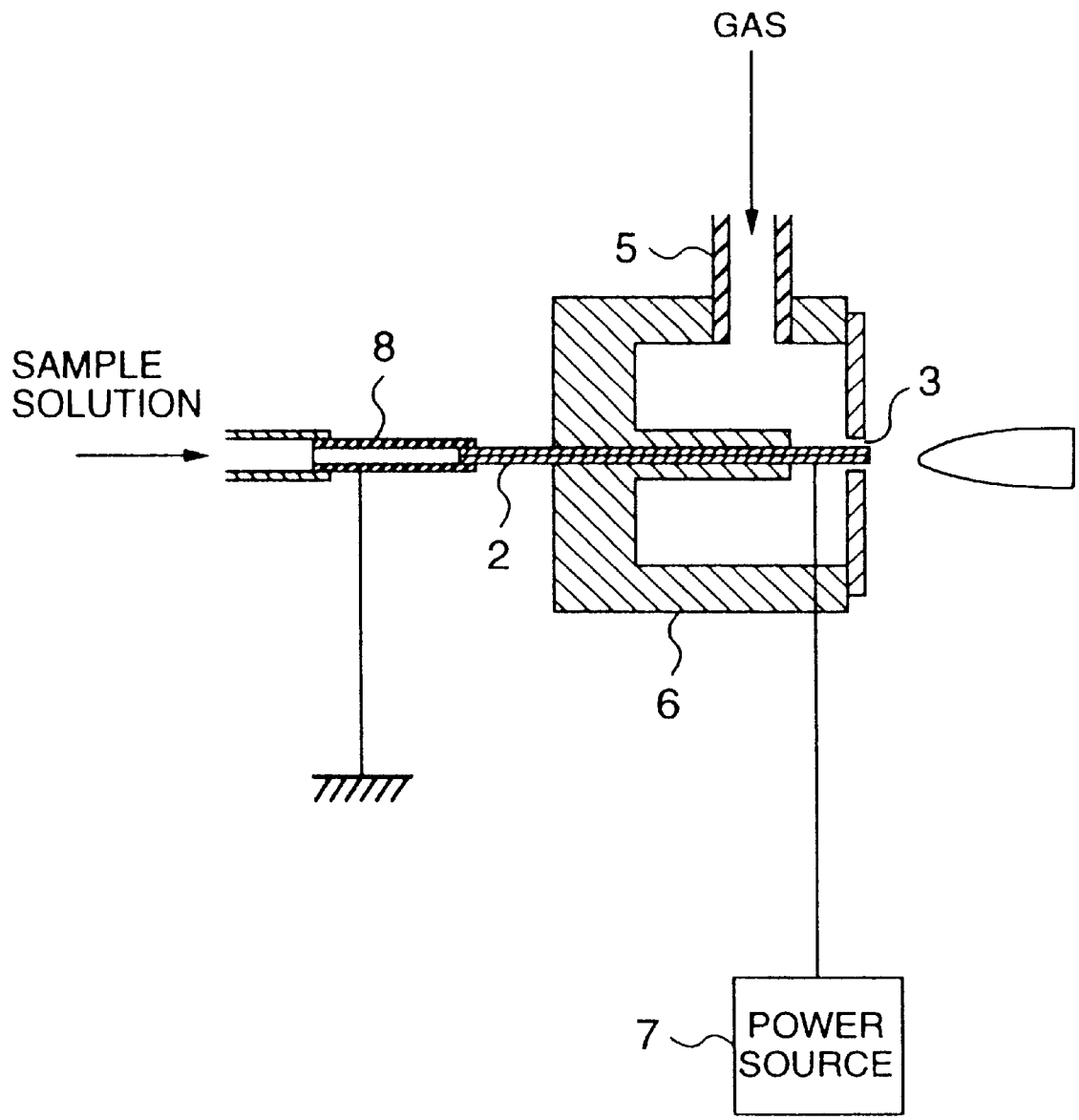
FIG. 10 is a cross sectional view, partly in block diagram, showing a structure of an ion source according to another embodiment of the present invention.

Referring to FIG. 10, there is shown a cross sectional view, partly in block diagram, of an ion source according to another embodiment of the present invention. Aluminium is deposited onto an outer surface of a tip with 5 mm length of a fused-silica capillary (its inner diameter is 0.01 mm, and its outer diameter is 0.05 mm), and a suitable voltage is applied to the tip of the capillary 2 by a power source 7. As stated in the description with respect to FIG. 4, in order to produce ions efficiently, it is necessary to generate an electric field having the intensity which is equal to or higher than a certain level. In the present embodiment, a voltage applied to an electrode can be set to a lower level than that in the above-mentioned embodiment shown in FIG. 2. In the present embodiment, since an electric potential of an ion source body 6 can be set to the ground level, the safety during operation of the system is very high.

Figure 11:
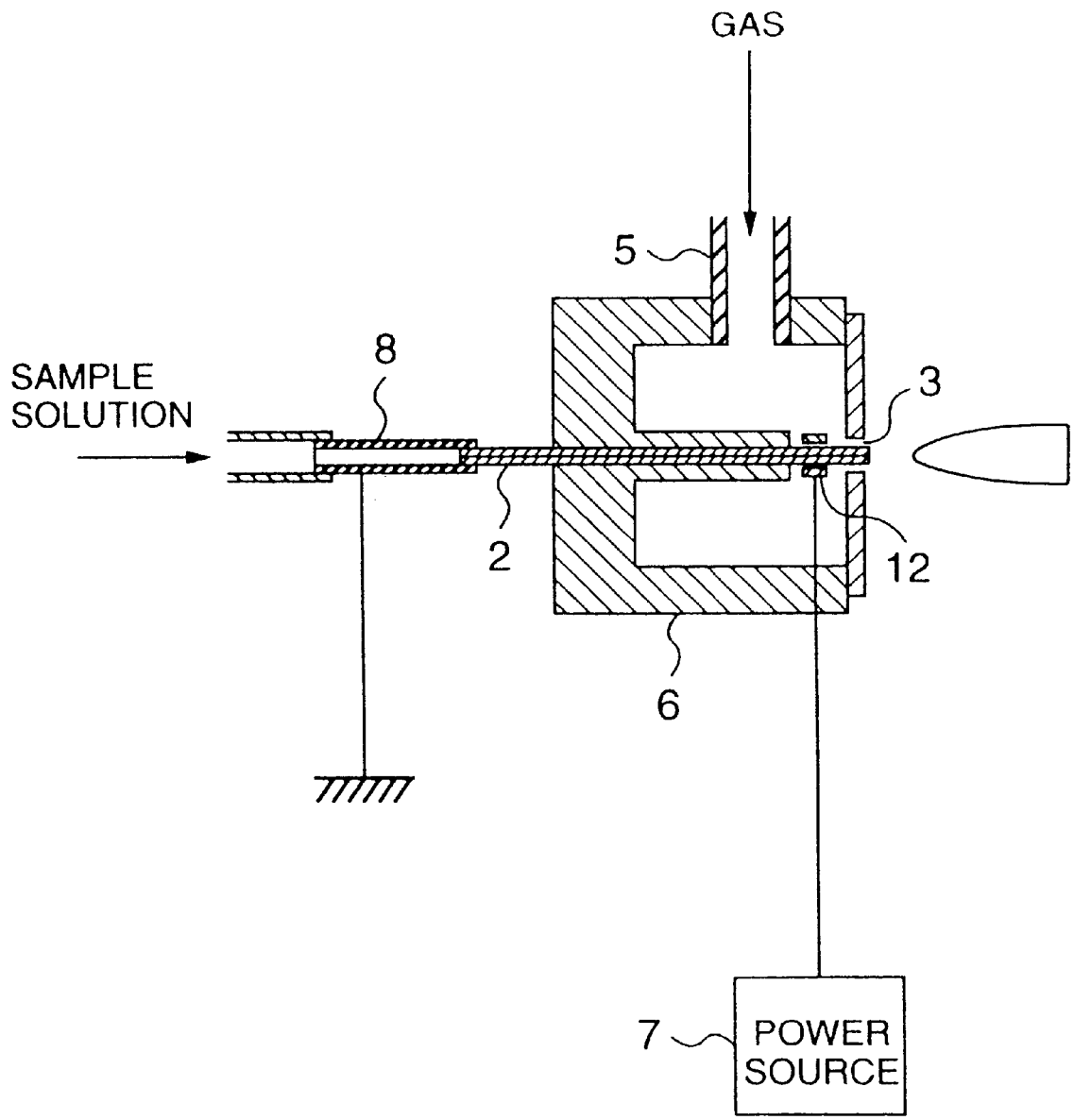
FIG. 11 is a cross sectional view, partly in block diagram, showing a structure of an ion source according to still another embodiment of the present invention.

Referring to FIG. 11, there is shown a cross sectional view, partly in block diagram, of an ion source according to still another embodiment of the present invention. A capillary 2 made of resin is inserted through a tubular electrode 12, and a suitable voltage is applied to the electrode 12 by a power source 7. The capillary 2 made of resin is adhered to the tubular electrode 12 by insulating adhesive. If a sufficiently high voltage is applied to the tubular electrode 12, the tubular electrode 12 is not necessarily aligned coaxially with the capillary 2. However, in the case where the tubular electrode 12 is aligned substantially coaxially with the capillary 2, the ion production is carried out with a lower applied voltage. In addition, similarly, if the sufficiently high voltage is applied to the tubular electrode 12, the electrode 12 does not need to have necessarily the tubular shape. The applied voltage has only to be much lower in the case where the electrode 12 is arranged to this side with respect to the tip of the capillary 2 as compared with the case where the electrode 2 is not arranged to this side with respect to the tip of the capillary 2.

Figure 12:
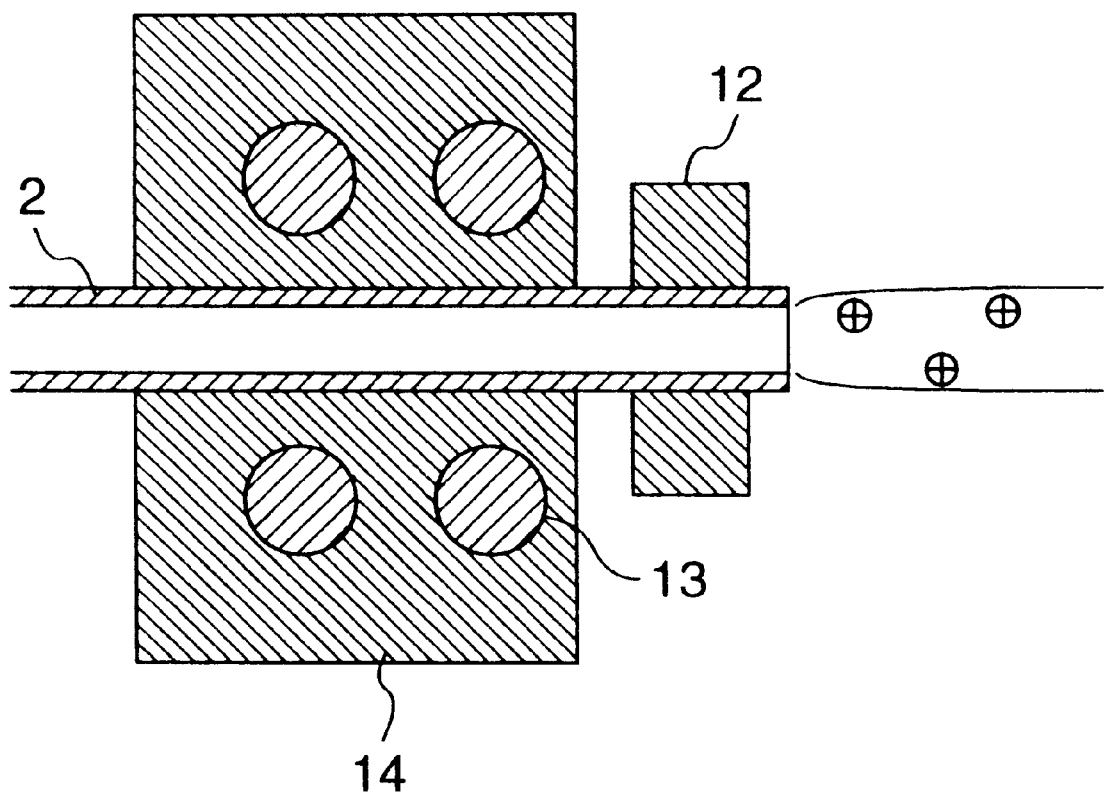
FIG. 12 is a cross sectional view, partly in block diagram, showing a structure of an ion source according to yet another embodiment of the present invention.

Referring to FIG. 12, there is shown a cross sectional view of an ion source according to yet another embodiment of the present invention. A fused-silica capillary 2 is heated by a heating block 14 which is heated in turn by a heater 13. Therefore, the liquid which has been introduced into the capillary 2 is sprayed by assistance of heating. The droplets which have been produced in the capillary 2 by the spray are charged positive or negative by application of an electric field generated through an electrode 12, thereby producing the charged droplets and the ions. For heating of the liquid, an infrared laser or a lamp may be employed.

Figure 13:
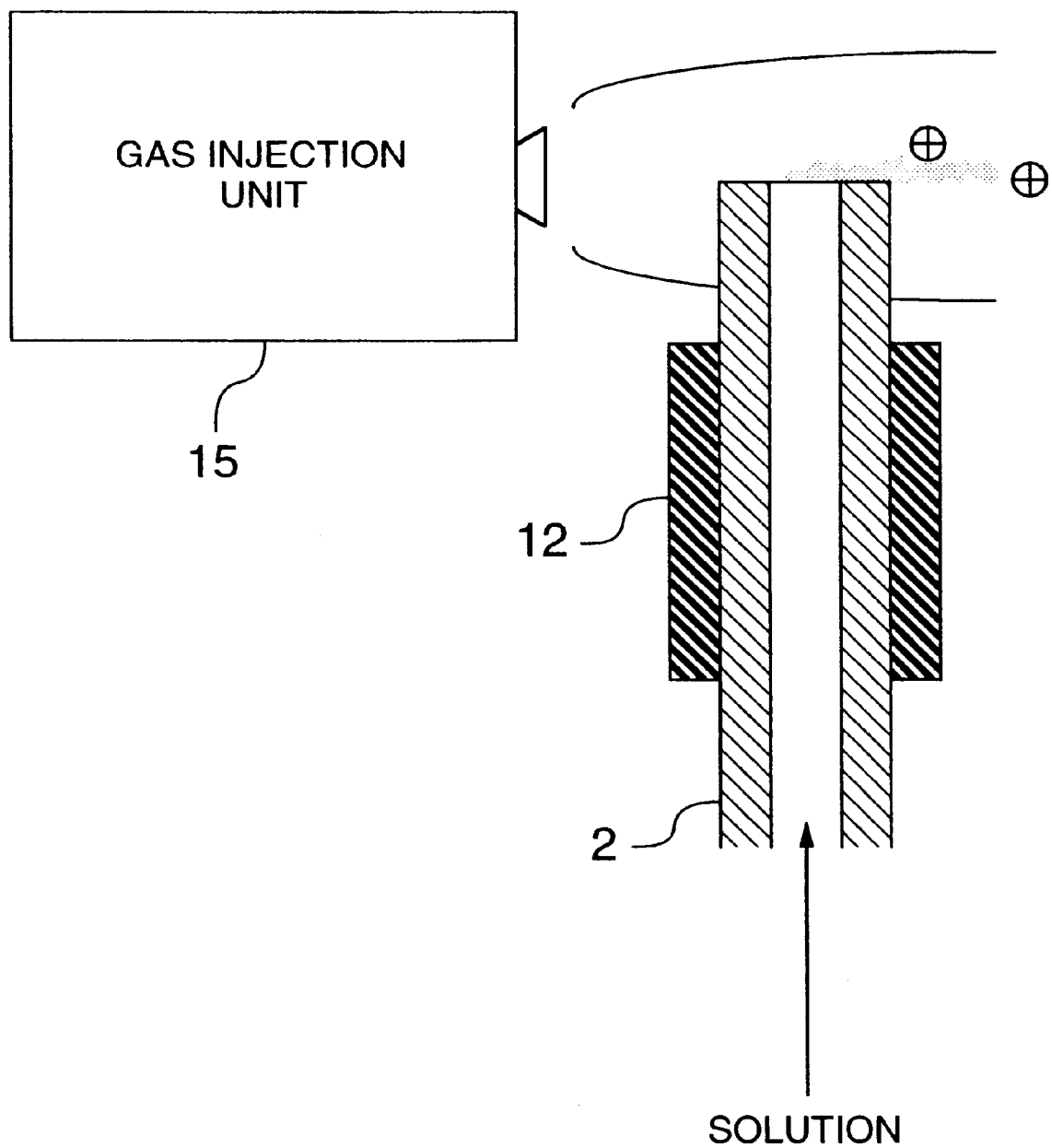
FIG. 13 is a cross sectional view, partly in block diagram, showing a structure of an ion source according to a further another embodiment of the present invention.

Referring to FIG. 13, there is shown a cross sectional view of an ion source according to a further embodiment of the present invention. The liquid which has been introduced into a fused-silica capillary 2 is sprayed in a transverse direction at a tip of the capillary 2 by assistance of the gas flow which is produced by a gas injection unit 15. In this case, while the relatively larger charged droplets are produced, the positional adjustment of the capillary 2 can be carried out in a very simple manner. In particular, in the case where there is no need of producing ions, and only the production of the droplets is enough, the present embodiment provides a very simple system for producing charged droplets.

Figure 14:
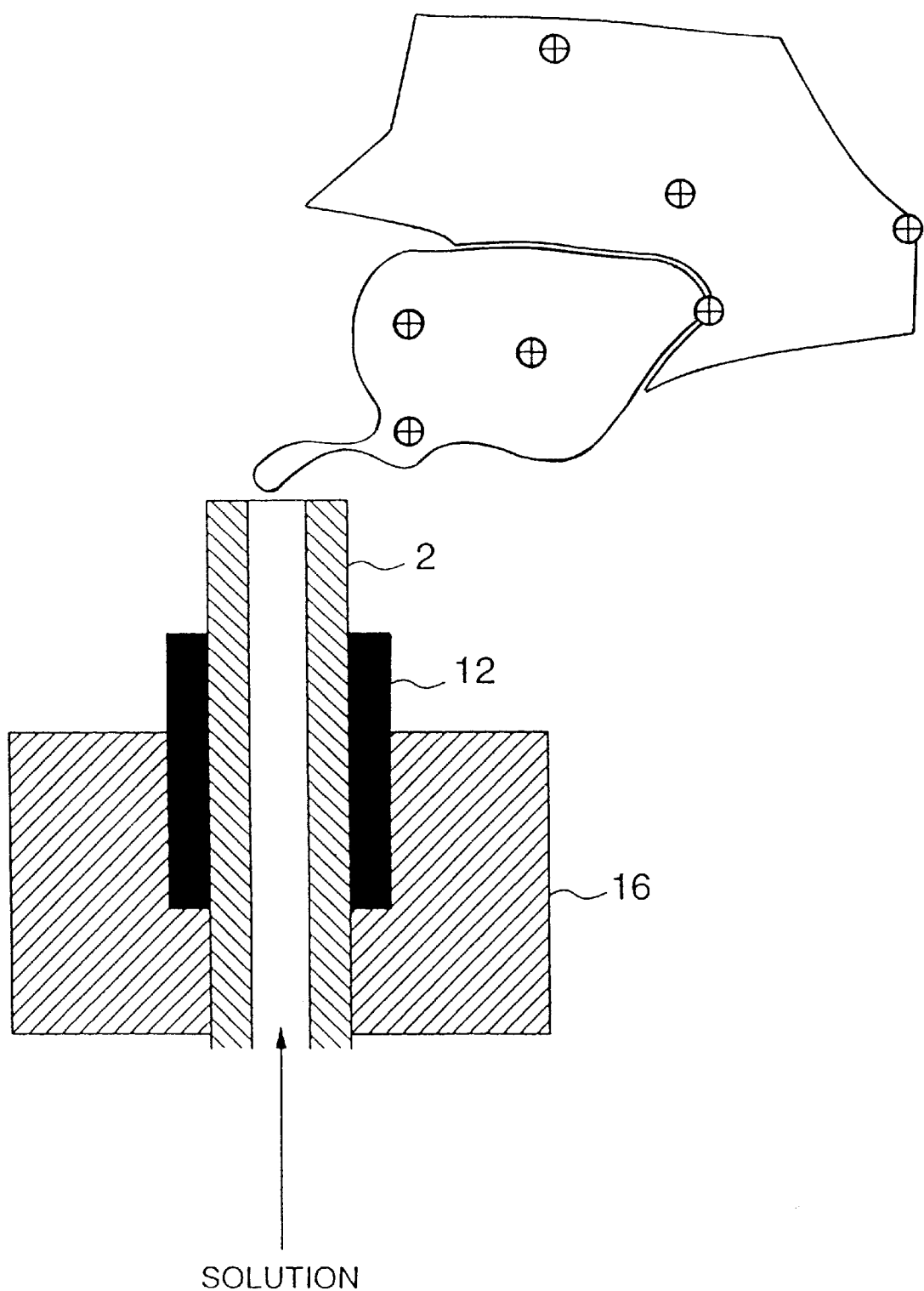
FIG. 14 is a cross sectional view, partly in block diagram, showing a structure of an ion source according to an even further another embodiment of the present invention.

Referring to FIG. 14, there is shown a cross sectional view of an ion source according to an even further embodiment of the present invention. The liquid which has been introduced into a fused-silica capillary 2 is converted into droplets by a ultrasonic vibrator 16. These droplets are charged positive or negative when producing the droplets by application of an electric field generated through an electrode 12. The sprayed gases charged positive or negative are spatially widely diffused. Each of the above-mentioned embodiments shown in FIGS. 12 to 14, respectively, has an advantage that the ions can be produced without using either a gas bomb or a compressor.

Figure 15:
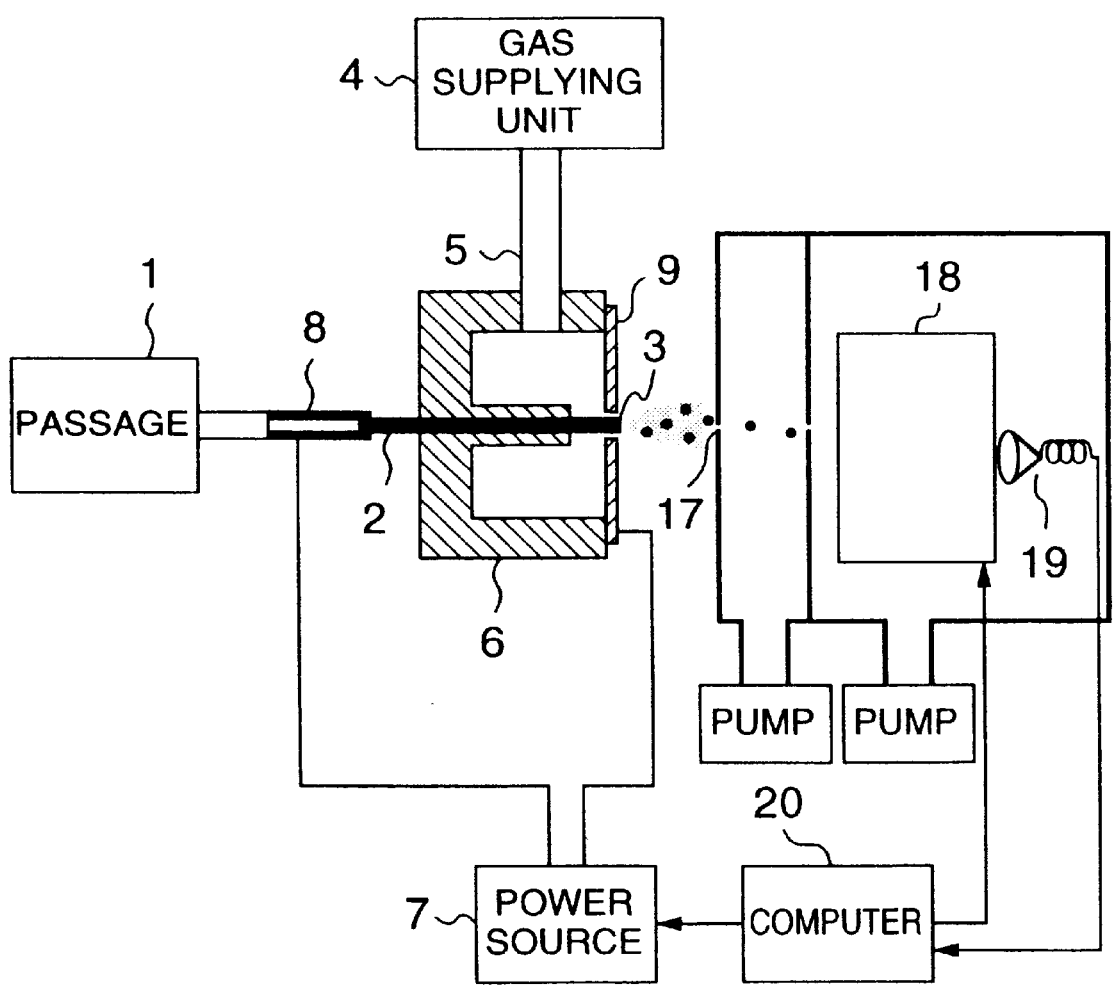
FIG. 15 is a cross sectional view, partly in block diagram, showing a structure of a mass spectrometer according to an embodiment of the present invention.

Referring to FIG. 15, there is shown a cross sectional view, partly in block diagram, of a structure of a mass spectrometer according to an embodiment of the present invention. The liquid is introduced into a capillary 2 at a fixed flow rate through a passage 1. A tip of the capillary 2 is substantially coaxially inserted into an orifice 3. Nitrogen gas which has been supplied from a gas supplying unit 4 is introduced into an ion source body 6 through a gas introducing conduit 5 so as to be discharged through the orifice 3 to the outside. A suitable voltage is applied to a metallic orifice plate 9 by a power source 7. As a result, an electric field is applied to the liquid which has reached the tip of the capillary 2. The liquid to which the electric field is applied is sprayed to the outside at an atmospheric pressure by assistance of the gas flow generated through the orifice 3. In general, a uniform electric field is present between the metallic orifice plate 9 through which the sprayed gas is produced and an orifice 17 in an inlet port of a mass spectrometry unit 18. Both the ions and the charged droplets which have been produced in the sprayed gas are introduced into a vacuum through the orifice 17 in the inlet port of the mass spectrometry unit 18, and then are subjected to the mass separation by application of an electric field or a magnetic field in the mass spectrometry unit 18 installed in a high vacuum unit. The ions which have been subjected to the mass separation are detected by an ion detecting unit 19. An output signal outputted from ion detecting unit 19 is sent to a computer 20 in order to be analyzed. Both the power source 7 and the mass spectrometry unit 18 can be controlled by the computer 20. That is, the positive/negative ions which have been produced on the basis of an intermittent voltage signal generated by the power source 7 can be subjected to the mass separation synchronously with the ion production so as to be detected. For example, when an electric potential of a metallic conduit 8 is set to the ground level and a rectangular voltage signal with 1 kV amplitude is applied to the orifice plate 9 by the power source 7 so as to produce the positive/negative ions, the positive/negative ions can be analyzed synchronously with the ion production. In the case where the electric potentials of the capillary 2 or the metallic conduit 8 and the orifice 17 are set to the same electric potential so that no uniform electric field is present in a space when the sprayed gas is produced as well as in the case where an electric potential difference of about 200 V is generated therebetween, there is no problem for ion detection at all.

When setting an electric potential of the metallic conduit 8 to the ground level, an electric potential of the liquid which is caused to flow through the capillary 2 can be set to the ground level. Therefore, solution separating means such as a capillary electrophoresis system or a liquid chromatograph can be readily coupled to the passage 1.

Figure 16:
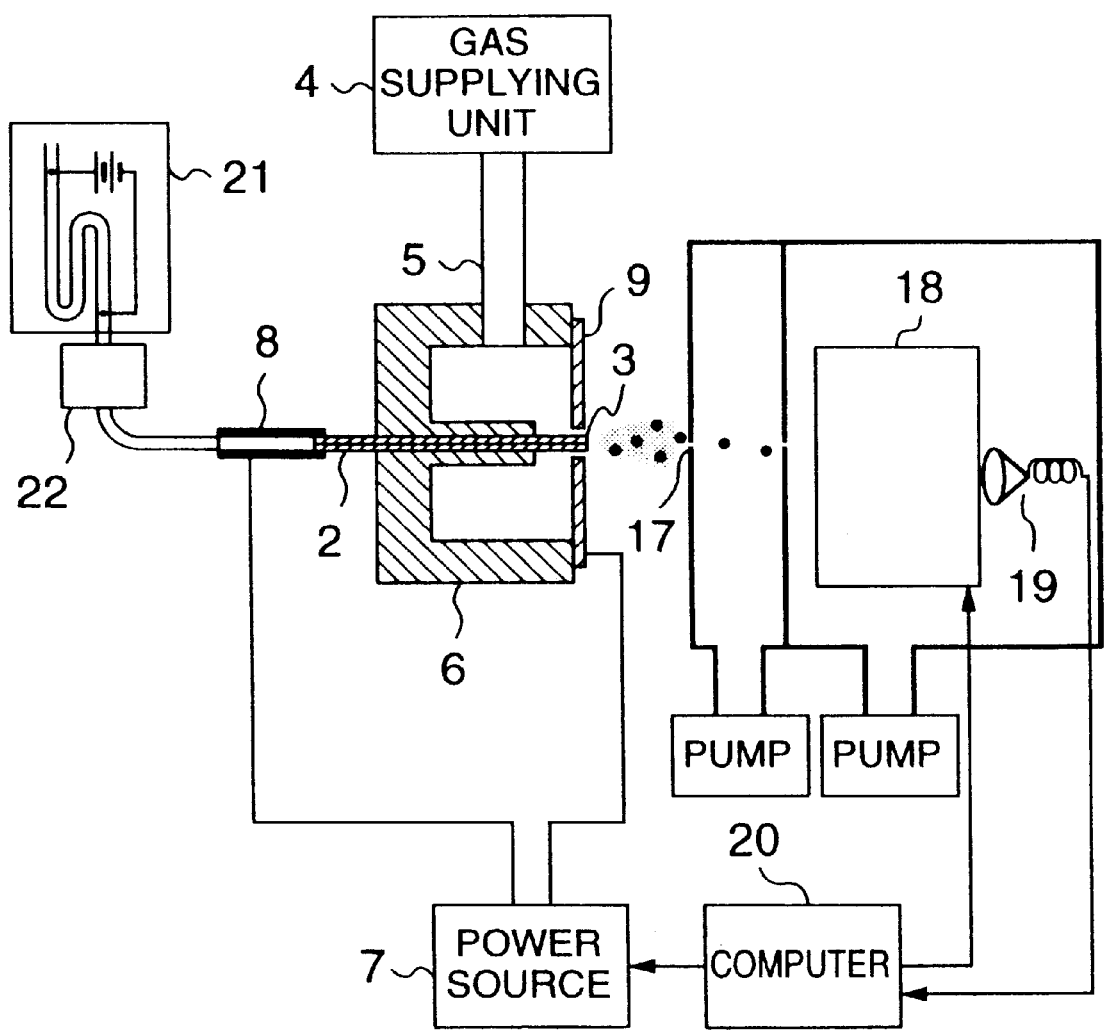
FIG. 16 is a cross sectional view, partly in block diagram, showing a structure of a capillary electrophoresis/mass spectrometer coupling system according to an embodiment of the present invention.

Referring to FIG. 16, there is shown a cross sectional view, partly in block diagram, of a structure of a capillary electrophoresis system/mass spectrometer coupling system of an embodiment of the present invention. A mixed solution is introduced into a capillary electrophoresis system 21, and then is electrophoresed by a high voltage applied across mutually opposite ends of a capillary 2 so as to be separated. The separated solution is introduced into the capillary 2 after having been detected in a detection unit 22. A tip of the capillary 2 is substantially coaxially inserted into an orifice 3. Nitrogen gas which has been supplied from a gas supplying unit 4 is introduced into an ion source body 6 through a gas introducing conduit 5 so as to be discharged through the orifice 3 to the outside in the form of a gas flow. An orifice plate 9 is made of metal, and a suitable voltage is applied to the metallic orifice plate 9 by a power source 7. The liquid which has reached a tip of the capillary 2 is sprayed to the outside at an atmospheric pressure by assistance of the gas flow. Both the ions and the charged droplets which have been produced in the sprayed gas are introduced into a vacuum through an orifice 17 in an inlet port of a mass spectrometry unit, and then are subjected to the mass separation by application of an electric field or a magnetic field in a mass spectrometry unit 18 installed in a high vacuum unit. The ions which have been subjected to the mass separation are detected by an ion detecting unit 19. An output signal outputted from the ion detecting unit 19 is sent to a computer 20 in order to be analyzed. Both the power source 7 and the mass spectrometry unit 18 can be controlled by the computer 20. That is, the positive/negative ions which have been produced on the basis of an intermittent voltage generated by the power source 7 can be subjected to the mass separation synchronously with the ion production so as to be detected in the ion detection unit 19. For example, when an electric potential of a metallic conduit 8 is set to the ground level, and also a rectangular voltage signal with 1 kV amplitude is applied to the orifice plate 9 by the power source 7 so as to produce the positive/negative ions, the positive/negative ions can be analyzed synchronously with the ion production. In the case where the electric potentials of the capillary 2 or the metallic conduit 8 and the orifice 17 are set to the same electric potential so that no electric field is present in a space where the sprayed gas is produced as well as in the case where an electric potential difference of about 200 V is generated therebetween, there is no problem for ion detection at all. For the mass spectrometry unit 18, all kinds of mass spectrometry units such as a quadrupole mass spectrometer, a quadrupole ion trap mass spectrometer, a magnetic sector type mass spectrometer, a time-of-flight mass spectrometer, and a Fourier transform mass spectrometer may be employed. The electric potential of the metallic conduit 8 is set to the ground level, whereby the electric potential of the mixed solution in the capillary electrophoresis system 21 can also be set to the ground level. Therefore, the capillary electrophoresis system 21 can be operated without any difficulty in the separation of the mixed solution, and hence the high sensitivity separation analysis of the mixed solution is realized online. Even if the solution separating means such as a liquid chromatograph is used instead of the capillary electrophoresis system 21, the high sensitivity separation analysis of the mixed solution is realized online in a completely similar manner.

Figure 17:
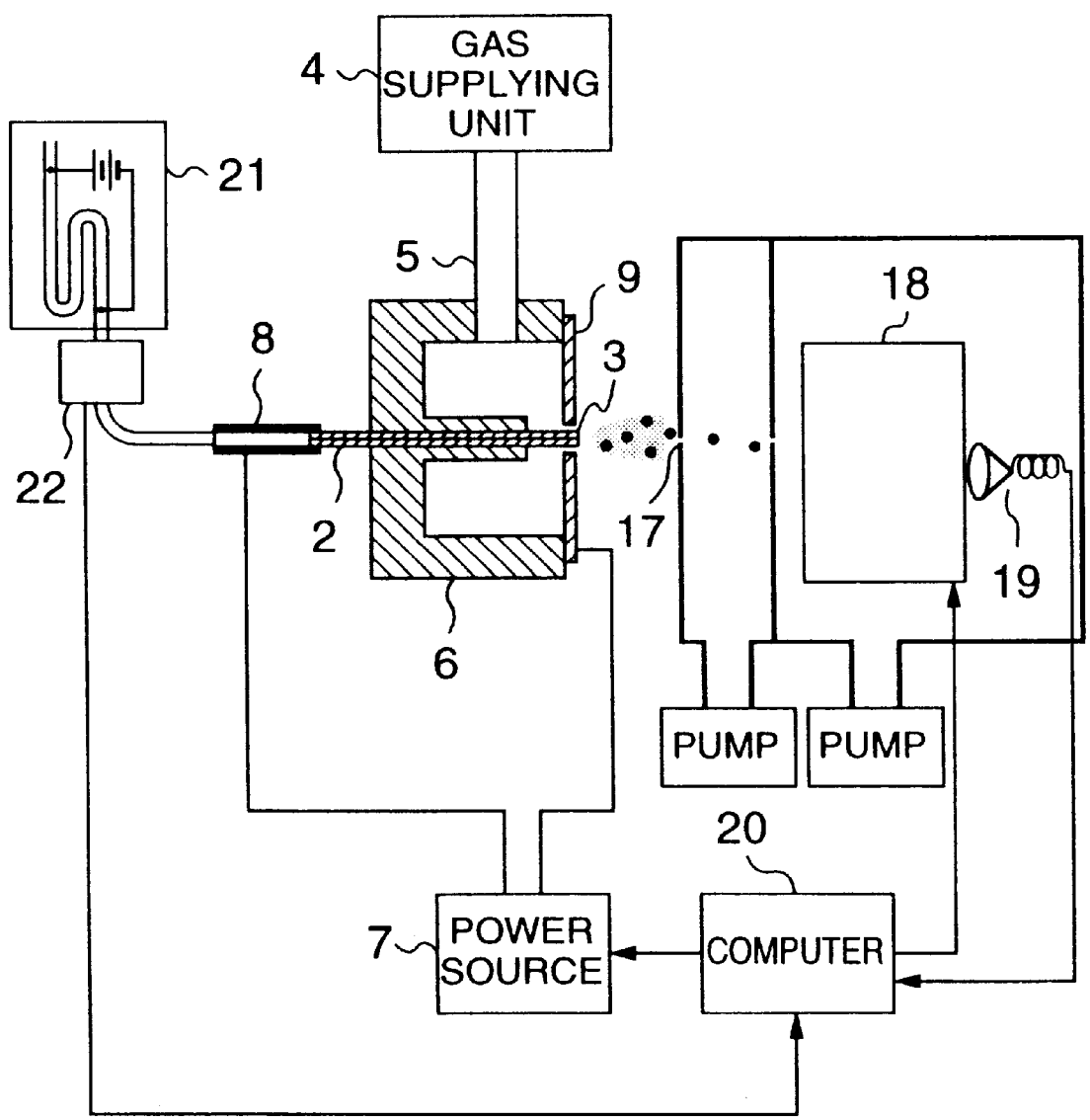
FIG. 17 is a cross sectional view, partly in block diagram, showing a structure of a capillary electrophoresis/mass spectrometer coupling system according to another embodiment of the present invention.

Referring to FIG. 17, there is shown a cross sectional view, partly in block diagram, of a structure of a capillary electrophoresis/mass spectrometer coupling system according to an embodiment of the present invention. A mixed solution is introduced into a capillary electrophoresis system 21, and is electrophoresed by a high voltage applied across both ends of a fused-silica capillary 2 so as to be separated. The separated solution is then introduced into the capillary 2 through a metallic conduit 8 having an electric potential set to the ground level after having been detected in a detection unit 22. A tip of the capillary 2 is substantially coaxially inserted into an orifice 3. Nitrogen gas which has been supplied from a gas supplying unit 4 is introduced into an ion source body 6 through a gas introducing conduit 5 so as to be discharged through the orifice 3 to the outside in the form of a gas flow. An orifice plate 9 is made of metal, and a suitable voltage is applied to the metallic orifice plate 9 by a power source 7. The liquid which has reached the tip of the capillary 2 is sprayed to the outside at an atmospheric pressure by assistance of the gas flow. Both the ions and the charged droplets which have been produced in the sprayed gas are introduced into a vacuum through an orifice 17 in an inlet port of a mass spectrometry unit 18, and then are subjected to the mass separation by application of an electric field or a magnetic field in the mass spectrometry unit 18 installed in a high vacuum unit. The ions which have been subjected to the mass separation are detected by an ion detecting unit 19. An output signal outputted from the ion detecting unit 19 is sent to a computer 20. In response thereto, an instruction to control the operation of both the power source 7 and the mass spectrometry unit 18 is issued from the computer 20. Then, an output signal outputted from the ion detecting unit 19 is sent to the computer 20 in order to be analyzed.

In the materials which are separated by the capillary electrophoresis system 21, there are contained materials which become the positive ions by the spray and materials which become the negative ions by the spray. For this reason, for example, even when the materials to become the negative ions are separated, if only the positive ions cannot be produced by the spray or only the positive ions cannot be analyzed, such materials cannot be analyzed. Then, while the separated materials are sprayed through the capillary 2, the polarity of the voltage applied to the orifice plate 9 is reversed so as to analyze both the positive ions and the negative ions. Since the electric potential of the metallic conduit 8 is set to the ground level, analysis of the positive/negative ions does not influence the capillary electrophoresis system 21 at all. Even if the solution separating means such as a liquid chromatograph is used instead of the capillary electrophoresis system 21, the high sensitivity separation analysis of the mixed solution is realized online in a completely similar manner.

Figure 18:
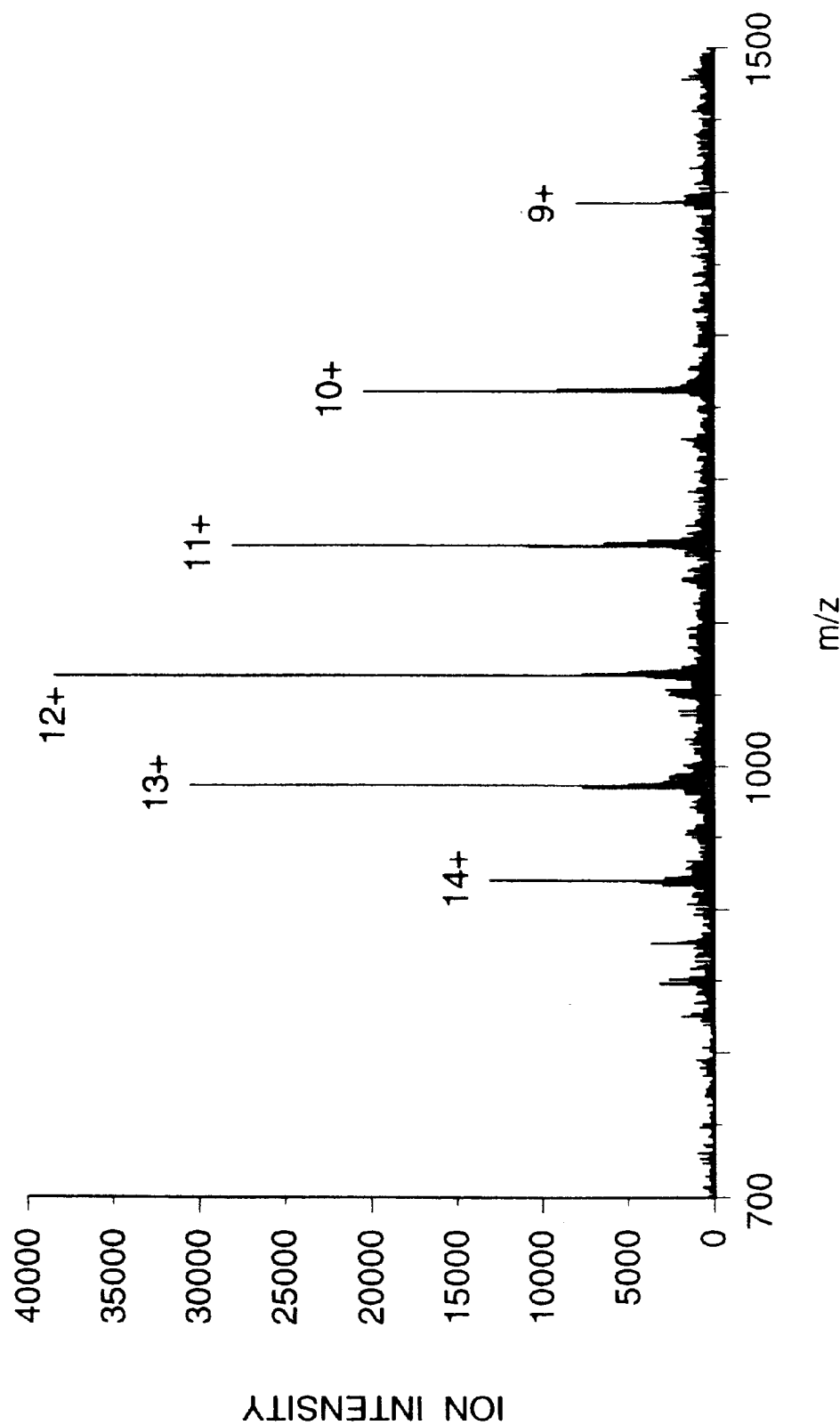
FIG. 18 is a mass spectrum which is obtained from a cytochrome-C solution containing strong acid (trifluoroacetic acid) added thereto.

Referring to FIG. 18, there is shown a mass spectrum which is obtained from the experimental results in which when setting an applied voltage to 1 kV, ions which are produced from a cytochrome-C solution with 10 $\mu$mol/l containing strong acid added thereto are subjected to the mass spectrometry. A solvent is 50% methyl alcohol liquid containing 0.1% TFA (trifluoroacetic acid) added thereto. This solution is introduced into the capillary at a flow rate of 30 $\mu$l/min, and the ions which have been produced by the spray using the gas flow of the sonic velocity are analyzed by a quadrupole ion trap mass spectrometer. From FIG. 18, it is shown that a series of multiply-charged ions ranging from a 9+ ion to a 14+ ion are clearly detected with a 12+ ion, in which a cytochrome-C molecule has twelve protons added thereto, as center.

In the conventional electrospray ionization method and ion spray ionization method, a suitable voltage is directly applied to the sample solution, and the sample solution is sprayed by the electrostatic force so as to be ionized. For this reason, if strong acid such as TFA is added to the solution, a current is caused to flow through the solution, and hence it is difficult to spray the solution. As a result, the production of ions also becomes difficult. However, in the sonic spray ionization method, since a voltage is not directly applied to the solution, the production of ions is not impeded at all.

Figure 19:
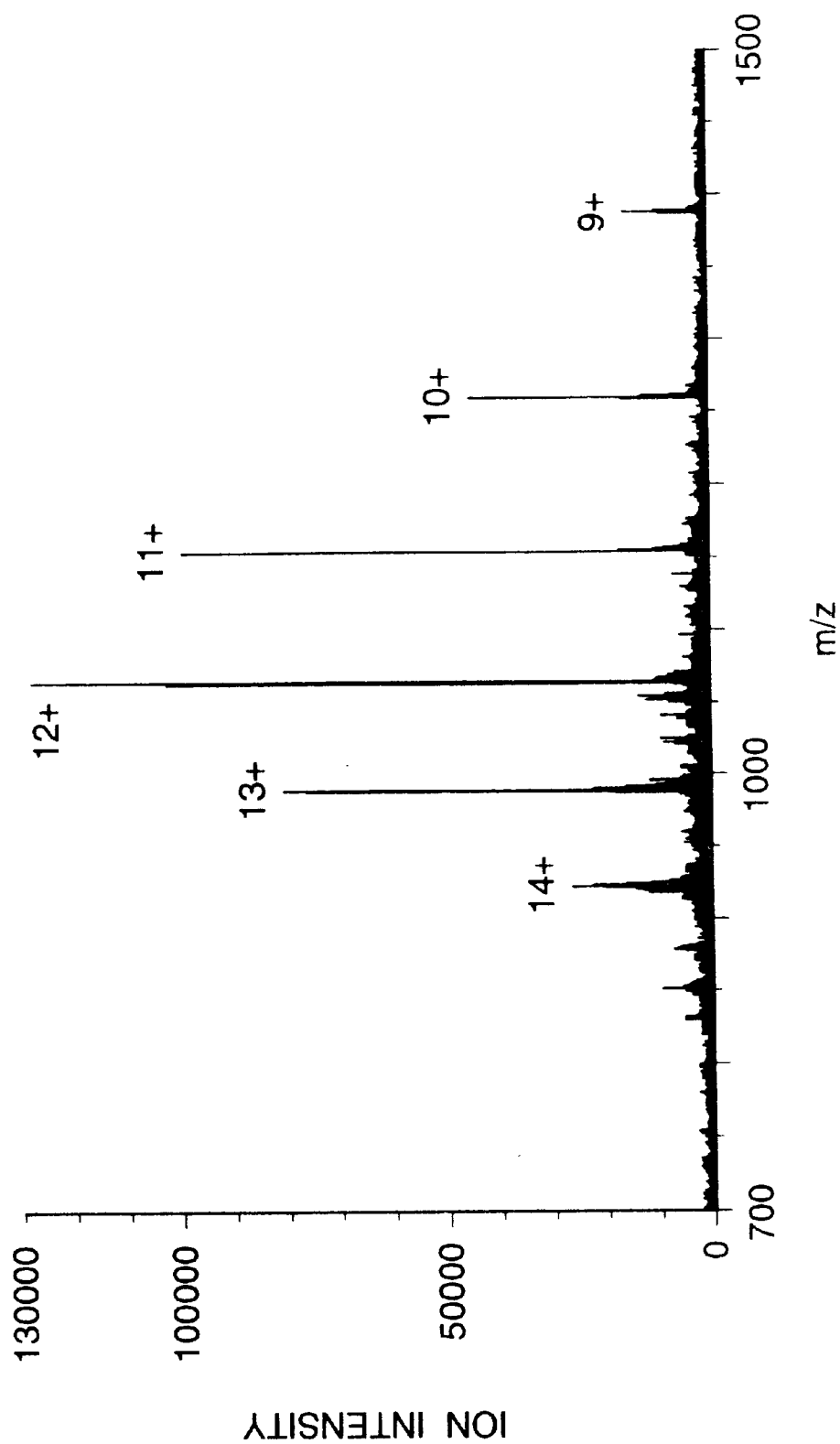
FIG. 19 is a mass spectrum which is obtained from a cytochrome-C solution containing weak acid (acetic acid) added thereto.

Referring to FIG. 19, there is shown a mass spectrum which is obtained from the experimental results in which the ions which are produced from a cytochrome-C solution with 10 $\mu$mol/l concentration containing weak acid added thereto are subjected to the mass spectrometry. A solvent is 48% methyl alcohol liquid containing 5% acetic acid added thereto. In this connection, measurement conditions are the same as those in FIG. 18. When comparing the experimental results of FIG. 18 with the experimental results of FIG. 19, it is understood that the ion intensity obtained from the solution containing strong acid added thereto is about ⅓ of that obtained from the solution containing weak acid added thereto, but the S/N ratio of the former is approximately equal to that of the latter. Therefore, even when a strong acid solution is added to the sample, there arises no problem in the present ionization method.

As set forth hereinabove, according to the ion source and the mass spectrometer employing the same of the present invention, the higher stability and reproducibility of the ion production can be obtained as compared with both the electrospray ionization method and the ion spray ionization method which utilize the electrostatic spray phenomenon. Since even if the spray is restarted after having been temporarily stopped, the ion production is reproduced the operationalization of the ion source is very high because only the gas spray of the solution is utilized in the ion production. In addition, since the electrostatic spray is not utilized in the ion production at all, the materials contained in the strong acid solution can also be ionized.

While the present invention has been particularly shown and described with reference to the preferred embodiments thereof, it will be understood that the various changes and modifications will occur to those skilled in the art without departing from the scope and true spirit of the invention. The scope of the invention is therefore to be determined solely by the appended claims.

What is claimed is:

1. A nebulizer comprising:

a passage through which a liquid flows, the passage including a capillary having an open tip, the liquid flowing through the capillary out of the open tip of the capillary;

a gas passage which forms a gas flow around the open tip of the capillary, the gas flow spraying the liquid flowing out of the open tip of the capillary;

a first electrode which contacts the liquid flowing in the passage and applies an electric potential to the liquid flowing in the passage; and a second electrode disposed around the capillary near the open tip of the capillary, the second electrode being downstream from the first electrode with respect to a direction in which the liquid flows in the passage, there being no gap extending downstream from the open tip of the capillary to the second electrode in a direction in which the liquid flows out of the open tip of the capillary, the second electrode being electrically isolated from the liquid flowing in the capillary and applying an electric field to the liquid flowing in the capillary.

2. A nebulizer comprising:

a capillary through which a liquid flows, the capillary being made of an electrically insulating material and having a tip out of which the liquid flows;

a conduit through which the liquid flowing in the capillary is introduced into the capillary, the conduit having a metallic inner surface which contacts the liquid which is introduced into the capillary;

a metallic orifice disposed around the capillary near the tip of the capillary;

a gas supplier which supplies a gas to the metallic orifice so that the gas flows between the metallic orifice and an outer surface of the capillary towards the tip of the capillary; and a voltage source which applies an electric voltage between the metallic inner surface of the conduit and the metallic orifice.

3. A nebulizer comprising:

a passage through which a liquid flows, the passage including a capillary having an open tip, the liquid flowing through the capillary out of the open tip of the capillary;

a gas passage which forms a gas flow around the open tip of the capillary, the gas flow spraying the liquid flowing out of the open tip of the capillary;

a first electrode which contacts the liquid flowing in the passage and applies an electric potential to the liquid flowing in the passage; and a second electrode disposed around the capillary near the open tip of the capillary, the second electrode being downstream from the first electrode with respect to a direction in which the liquid flows in the passage, there being no gap extending downstream from the open tip of the capillary to the second electrode in a direction in which the liquid flows out of the open tip of the capillary, the second electrode being electrically isolated from the liquid flowing in the capillary and applying an electric field to the liquid flowing in the capillary;

wherein the gas flow has a characteristic value F/S between 250 meters/second (m/s) and 1200 m/s at a position near the tip of the capillary, where F is a flow rate of the gas at standard conditions (20° C., 1 atmosphere), and S is an area of a cross section of the gas flow at the position near the tip of the capillary.

4. An ion source comprising:

a passage through which a liquid flows, the passage including a capillary having an open tip, the liquid flowing through the capillary out of the open tip of the capillary;

a gas passage which forms a gas flow around the open tip of the capillary, the gas flow spraying the liquid flowing out of the open tip of the capillary;

a first electrode which contacts the liquid flowing in the passage and applies an electric potential to the liquid flowing in the passage; and a second electrode disposed around the capillary near the open tip of the capillary, the second electrode being downstream from the first electrode with respect to a direction in which the liquid flows in the passage, there being no gap extending downstream from the open tip of the capillary to the second electrode in a direction in which the liquid flows out of the open tip of the capillary, the second electrode being electrically isolated from the liquid flowing in the capillary and applying an electric field to the liquid flowing in the capillary.

5. An ion source comprising:

a capillary through which a liquid flows, the capillary being made of an electrically insulating material and having a tip out of which the liquid flows;

a conduit through which the liquid flowing in the capillary is introduced into the capillary, the conduit having a metallic inner surface which contacts the liquid which is introduced into the capillary;

a metallic orifice disposed around the capillary near the tip of the capillary;

a gas supplier which supplies a gas to the metallic orifice so that the gas flows between the metallic orifice and an outer surface of the capillary towards the tip of the capillary; and a voltage source which applies an electric voltage between the metallic inner surface of the conduit and the metallic orifice.

6. An ion source comprising:

a passage through which a liquid flows, the passage including a capillary having an open tip, the liquid flowing through the capillary out of the open tip of the capillary;

a gas passage which forms a gas flow around the open tip of the capillary, the gas flow spraying the liquid flowing out of the open tip of the capillary;

a first electrode which contacts the liquid flowing in the passage and applies an electric potential to the liquid flowing in the passage; and a second electrode disposed around the capillary near the open tip of the capillary, the second electrode being downstream from the first electrode with respect to a direction in which the liquid flows in the passage, there being no gap extending downstream from the open tip of the capillary to the second electrode in a direction in which the liquid flows out of the open tip of the capillary, the second electrode being electrically isolated from the liquid flowing in the capillary and applying an electric field to the liquid flowing in the capillary;

wherein the gas flow has a characteristic value F/S between 250 meters/second (m/s) and 1200 m/s at a position near the tip of the capillary, where F is a flow rate of the gas at standard conditions (20° C., 1 atmosphere), and S is an area of a cross section of the gas flow at the position near the tip of the capillary.

7. A mass spectrometer comprising:

a passage through which a sample solution flows, the passage including a capillary having an open tip, the sample solution flowing through the capillary out of the open tip of the capillary;

a gas passage which forms a gas flow around the open tip of the capillary, the gas flow spraying the sample solution flowing out of the open tip of the capillary;

a first electrode which contacts the sample solution flowing in the passage and applies an electric potential to the sample solution flowing in the passage;

a second electrode disposed around the capillary near the open tip of the capillary, the second electrode being downstream from the first electrode with respect to a direction in which the sample solution flows in the passage, there being no gap extending downstream from the open tip of the capillary to the second electrode in a direction in which the sample solution flows out of the open tip of the capillary, the second electrode being electrically isolated from the sample solution flowing in the capillary and applying an electric field to the sample solution flowing in the capillary; and an analyzer which analyzes a mass of gaseous ions formed from the sample solution sprayed by the gas flow.

8. A mass spectrometer comprising:
a capillary through which a sample solution flows, the capillary being made of an electrically insulating material and having a tip out of which the sample solution flows;
a conduit through which the sample solution flowing in the capillary is introduced into the capillary, the conduit having a metallic inner surface which contacts the sample solution which is introduced into the capillary;
a metallic orifice disposed around the capillary near the tip of the capillary;
a gas supplier which supplies a gas to the metallic orifice so that the gas flows between the metallic orifice and an outer surface of the capillary towards the tip of the capillary and sprays the sample solution which flows out of the tip of the capillary;
a voltage source which applies an electric voltage between the metallic inner surface of the conduit and the metallic orifice; and
an analyzer which analyzes a mass of gaseous ions formed from the sample solution sprayed by the gas.

9. A mass spectrometer comprising:
a passage through which a sample solution flows, the passage including a capillary having an open tip, the sample solution flowing through the capillary out of the open tip of the capillary;
a gas passage which forms a gas flow around the open tip of the capillary, the gas flow spraying the sample solution flowing out of the open tip of the capillary;
a first electrode which contacts the sample solution flowing in the passage and applies an electric potential to the sample solution flowing in the passage;
a second electrode disposed around the capillary near the open tip of the capillary, the second electrode being downstream from the first electrode with respect to a direction in which the sample solution flows in the passage, there being no gap extending downstream from the open tip of the capillary to the second electrode in a direction in which the sample solution flows out of the open tip of the capillary, the second electrode being electrically isolated from the sample solution flowing in the capillary and applying an electric field to the sample solution flowing in the capillary; and
an analyzer which analyzes a mass of gaseous ions formed from the sample solution sprayed by the gas flow;
wherein the gas flow has a characteristic value F/S between 250 meters/second (m/s) and 1200 m/s at a position near the tip of the capillary, where F is a flow rate of the gas at standard conditions (20° C., 1 atmosphere), and S is an area of a cross section of the gas flow at the position near the tip of the capillary.

10. A method for producing ions, comprising the steps of:
introducing a liquid into a passage so that the liquid flows through the passage, the passage including a capillary having an open tip, the liquid flowing through the capillary out of the open tip of the capillary;
supplying a gas to a gas passage so that the gas passage forms a gas flow around the open tip of the capillary, the gas flow spraying the liquid flowing out of the open tip of the capillary;
applying a first voltage to a first electrode which contacts the liquid flowing in the passage, thereby applying an electric potential to the liquid flowing in the passage; and
applying a second voltage to a second electrode disposed around the capillary near the open tip of the capillary, the second electrode being downstream from the first electrode with respect to a direction in which the liquid flows in the passage, there being no gap extending downstream from the open tip of the capillary to the second electrode in a direction in which the liquid flows out of the open tip of the capillary, the second electrode being electrically isolated from the liquid flowing in the capillary, thereby applying an electric field to the liquid flowing in the capillary.

11. A method according to claim 10, wherein the gas flow has a characteristic value F/S between 250 meters/second (m/s) and 1200 m/s at a position near the tip of the capillary, where F is a flow rate of the gas at standard conditions (20° C., 1 atmosphere), and S is an area of a cross section of the gas flow at the position near the tip of the capillary.

* * * * *